(12) United States Patent
Gozani et al.

(10) Patent No.: US 12,364,862 B2
(45) Date of Patent: *Jul. 22, 2025

(54) APPARATUS AND METHOD FOR THE AUTOMATED CONTROL OF TRANSCUTANEOUS ELECTRICAL NERVE STIMULATION BASED ON CURRENT AND FORECASTED WEATHER CONDITIONS

(71) Applicant: Neurometrix, Inc., Waltham, MA (US)

(72) Inventors: Shai N. Gozani, Newton, MA (US);
Xuan Kong, Acton, MA (US)

(73) Assignee: Neurometrix, Inc., Waltham, MA (US)

( * ) Notice: Subject to any disclaimer, the term of this patent is extended or adjusted under 35 U.S.C. 154(b) by 388 days.

This patent is subject to a terminal disclaimer.

(21) Appl. No.: 17/374,294

(22) Filed: Jul. 13, 2021

(65) Prior Publication Data

US 2022/0001179 A1   Jan. 6, 2022

Related U.S. Application Data

(63) Continuation of application No. 15/990,994, filed on May 29, 2018, now Pat. No. 11,058,877.

(Continued)

(51) Int. Cl.
*A61N 1/36* (2006.01)
*A61N 1/04* (2006.01)
(Continued)

(52) U.S. Cl.
CPC ....... *A61N 1/36021* (2013.01); *A61N 1/0456* (2013.01); *A61N 1/0476* (2013.01);
(Continued)

(58) Field of Classification Search
CPC ............ A61N 1/36021; A61N 1/36034; A61N 1/3603; A61N 1/0456; A61N 1/0476;
(Continued)

(56) References Cited

U.S. PATENT DOCUMENTS 1,741,962 A   12/1929   Theodoropulos
4,290,431 A    9/1981   Herbert et al.
(Continued)

FOREIGN PATENT DOCUMENTS

CN   1665563   9/2005
CN   1919139   2/2007
(Continued)

OTHER PUBLICATIONS

Amazon, "Quell 2.0 Wearable Pain Relief Technology", Sep. 15, 2018.http://www.amazon/com/Quell-Wearable-Pain-Relief-Technology/dp/B07DHW2MJJ/ref=cm_cr_arp_d_product_top?ie=UTF8. Shown on p. 1. (Year: 2018).

(Continued)

*Primary Examiner* — Nadia A Mahmood
(74) *Attorney, Agent, or Firm* — Farber LLC

(57) ABSTRACT

Apparatus for transcutaneous electrical nerve stimulation in a user, the apparatus comprising: a stimulator for electrically stimulating at least one nerve with at least one stimulation pulse; a controller connected to the stimulator for controlling at least one characteristic of the at least one stimulation pulse; an analyzer for identifying the current and future presence of pain-altering patterns based on weather and/or environmental factors; and a processor connected to the analyzer and the controller for modulating the at least one characteristic of the at least one stimulation pulse according to the pain-altering patterns identified by the analyzer.

26 Claims, 13 Drawing Sheets

Related U.S. Application Data

(60) Provisional application No. 62/512,250, filed on May 30, 2017.

(51) Int. Cl.
  *A61N 1/22* (2006.01)
  *A61N 1/32* (2006.01)

(52) U.S. Cl.
  CPC ......... *A61N 1/0492* (2013.01); *A61N 1/3603* (2017.08); *A61N 1/36034* (2017.08); *A61N 1/0484* (2013.01); *A61N 1/22* (2013.01); *A61N 1/321* (2013.01)

(58) Field of Classification Search
  CPC ...... A61N 1/0492; A61N 1/0484; A61N 1/22; A61N 1/321
  See application file for complete search history.

(56) References Cited

U.S. PATENT DOCUMENTS

| | | | |
|---|---|---|---|
| D263,869 S | 4/1982 | Sumiyasu | |
| 4,503,863 A | 3/1985 | Katims | |
| 4,605,010 A | 8/1986 | McEwen | |
| 4,738,250 A | 4/1988 | Fulkerson et al. | |
| 4,777,711 A | 10/1988 | Forkner et al. | |
| 4,926,863 A | 5/1990 | Alt | |
| 4,989,605 A | 2/1991 | Rossen | |
| 5,048,523 A | 9/1991 | Yamasawa et al. | |
| 5,063,929 A | 11/1991 | Bartelt et al. | |
| D323,561 S | 1/1992 | Bartelt et al. | |
| 5,121,747 A | 6/1992 | Andrews | |
| 5,169,384 A | 12/1992 | Bosniak et al. | |
| D342,571 S | 12/1993 | Givens, Sr. | |
| D346,029 S | 4/1994 | Shalvi | |
| 5,350,414 A | 9/1994 | Kolen | |
| 5,429,589 A | 7/1995 | Cartmell et al. | |
| 5,479,939 A | 1/1996 | Ogino | |
| 5,487,759 A | 1/1996 | Bastyr et al. | |
| 5,562,718 A | 10/1996 | Palermo | |
| 5,806,522 A | 9/1998 | Katims | |
| D411,887 S | 7/1999 | Agarwala | |
| 5,919,149 A | 7/1999 | Allum | |
| 5,948,000 A | 9/1999 | Larsen et al. | |
| 5,954,758 A | 9/1999 | Peckham et al. | |
| 6,033,370 A | 3/2000 | Reinbold et al. | |
| 6,099,488 A | 8/2000 | Hung | |
| 6,132,387 A | 10/2000 | Gozani et al. | |
| 6,141,587 A | 10/2000 | Mower | |
| 6,148,233 A | 11/2000 | Owen et al. | |
| 6,161,044 A | 12/2000 | Silverstone | |
| D443,362 S | 6/2001 | Storp | |
| 6,266,558 B1 | 7/2001 | Gozani et al. | |
| D450,313 S | 11/2001 | Koinuma | |
| 6,430,450 B1 | 8/2002 | Bach-y-Rita et al. | |
| D462,772 S | 9/2002 | Lamping et al. | |
| 6,456,884 B1 | 9/2002 | Kenney | |
| 6,507,755 B1 | 1/2003 | Gozani et al. | |
| 6,611,789 B1 | 8/2003 | Darley | |
| 6,662,051 B1 | 12/2003 | Eraker et al. | |
| D484,984 S | 1/2004 | Takizawa et al. | |
| D534,871 S | 1/2007 | Larsen | |
| D541,042 S | 4/2007 | Andre et al. | |
| D547,454 S | 7/2007 | Hsieh | |
| D566,383 S | 4/2008 | Harris et al. | |
| D584,414 S | 1/2009 | Lash et al. | |
| D592,200 S | 5/2009 | Liu | |
| D598,556 S | 8/2009 | Chen | |
| D600,352 S | 9/2009 | Cryan | |
| D607,198 S | 1/2010 | Andre et al. | |
| D609,353 S | 2/2010 | Cryan | |
| 7,668,598 B2 | 2/2010 | Herregraven et al. | |
| D611,611 S | 3/2010 | Sachi et al. | |
| D615,526 S | 5/2010 | Andre et al. | |
| 7,720,548 B2 | 5/2010 | King | |
| 7,725,193 B1 | 5/2010 | Chu | |
| 7,787,946 B2 | 8/2010 | Stahmann et al. | |
| D625,016 S | 10/2010 | Potts et al. | |
| D625,829 S | 10/2010 | Arbesman et al. | |
| D629,115 S | 12/2010 | Robertson | |
| 7,887,493 B2 | 2/2011 | Stahmann et al. | |
| D636,881 S | 4/2011 | Clemens et al. | |
| D637,988 S | 5/2011 | Jinkinson | |
| 8,108,049 B2 | 1/2012 | King | |
| 8,121,702 B2 | 2/2012 | King | |
| 8,131,374 B2 | 3/2012 | Moore et al. | |
| D658,302 S | 4/2012 | Nixon | |
| 8,284,070 B2 | 10/2012 | Chaudhari et al. | |
| D677,792 S | 3/2013 | Vandiver | |
| D680,735 S | 4/2013 | Itabashi et al. | |
| 8,421,642 B1 | 4/2013 | McIntosh et al. | |
| D687,951 S | 8/2013 | Della Torre et al. | |
| D688,707 S | 8/2013 | Vincent et al. | |
| D704,848 S | 5/2014 | Thomas et al. | |
| D705,428 S | 5/2014 | Cheney et al. | |
| D712,045 S | 8/2014 | Thornton | |
| D712,052 S | 8/2014 | Thomas et al. | |
| D713,049 S | 9/2014 | Shah | |
| 8,825,175 B2 | 9/2014 | King | |
| 8,849,407 B1 * | 9/2014 | Danilov | A61N 1/0548 607/45 |
| D716,457 S | 10/2014 | Brefka et al. | |
| 8,862,238 B2 | 10/2014 | Rahimi et al. | |
| D716,963 S | 11/2014 | Yosef et al. | |
| 8,948,876 B2 * | 2/2015 | Gozani | A61N 1/37247 607/46 |
| D732,682 S | 6/2015 | Porat | |
| D735,873 S | 8/2015 | Brefka et al. | |
| 9,168,375 B2 | 10/2015 | Rahimi et al. | |
| 9,173,581 B2 | 11/2015 | Boettcher et al. | |
| D744,661 S | 12/2015 | Rizzi | |
| D745,975 S | 12/2015 | Igaue et al. | |
| D750,263 S | 2/2016 | Shigeno et al. | |
| D750,798 S | 3/2016 | Yosef et al. | |
| 9,282,287 B1 | 3/2016 | Marsh | |
| 9,282,897 B2 | 3/2016 | Ross, Jr. et al. | |
| D754,355 S | 4/2016 | Ganapathy et al. | |
| D754,973 S | 5/2016 | Danze et al. | |
| D757,292 S | 5/2016 | Chen | |
| D758,605 S | 6/2016 | Chen | |
| D758,606 S | 6/2016 | Chen | |
| D759,262 S | 6/2016 | Chen | |
| D759,263 S | 6/2016 | Chen | |
| D759,958 S | 6/2016 | Requa | |
| D762,628 S | 8/2016 | Yoon et al. | |
| D762,872 S | 8/2016 | Chen | |
| D767,775 S | 9/2016 | Gilmer et al. | |
| 9,452,287 B2 | 9/2016 | Rosenbluth et al. | |
| 9,474,898 B2 | 10/2016 | Gozani et al. | |
| D774,654 S | 12/2016 | Anderson | |
| D775,361 S | 12/2016 | Vosch et al. | |
| D778,453 S | 2/2017 | Knaus et al. | |
| D779,677 S | 2/2017 | Chen | |
| 9,561,397 B2 | 2/2017 | Zaki | |
| D784,544 S | 4/2017 | Dudkiewicz et al. | |
| D784,546 S | 4/2017 | Gordon | |
| D784,946 S | 4/2017 | Jun et al. | |
| D788,056 S | 5/2017 | Choi et al. | |
| 9,656,070 B2 | 5/2017 | Gozani et al. | |
| D789,546 S | 6/2017 | Matfus et al. | |
| D789,547 S | 6/2017 | Matfus et al. | |
| D791,333 S | 7/2017 | Wilson | |
| D792,363 S | 7/2017 | Kim et al. | |
| 9,700,724 B2 | 7/2017 | Liu et al. | |
| D794,331 S | 8/2017 | Grote | |
| 9,731,126 B2 | 8/2017 | Ferree et al. | |
| D798,170 S | 9/2017 | Toth et al. | |
| D801,542 S | 10/2017 | Anderson | |
| D802,780 S | 11/2017 | Hsu | |
| 9,827,420 B2 | 11/2017 | Ferree et al. | |
| D806,669 S | 1/2018 | Kangasmaa et al. | |
| D810,311 S | 2/2018 | Chen | |
| D810,843 S | 2/2018 | Karvandi | |
| D810,952 S | 2/2018 | Hsu | |

(56) References Cited

U.S. PATENT DOCUMENTS

| | | |
|---|---|---|
| D811,729 S | 3/2018 | Bysshe |
| D813,405 S | 3/2018 | Ho |
| D813,407 S | 3/2018 | Chen |
| D813,408 S | 3/2018 | Chen |
| D821,592 S | 6/2018 | Pham et al. |
| D828,569 S | 9/2018 | Mercuro |
| D829,182 S | 9/2018 | Li |
| 10,076,662 B2 | 9/2018 | Tuan |
| D830,565 S | 10/2018 | Xu |
| D831,017 S | 10/2018 | Choe et al. |
| D831,221 S | 10/2018 | Smith |
| D831,335 S | 10/2018 | Crease |
| D832,230 S | 10/2018 | Lee et al. |
| D834,719 S | 11/2018 | Theriot et al. |
| D836,788 S | 12/2018 | Peng |
| 10,154,922 B1 | 12/2018 | Perez et al. |
| D837,394 S | 1/2019 | Cryan et al. |
| 10,279,179 B2 | 5/2019 | Gozani |
| 10,335,595 B2 | 7/2019 | Ferree et al. |
| D857,910 S | 8/2019 | Cryan et al. |
| D861,903 S | 10/2019 | Cryan et al. |
| D861,904 S | 10/2019 | Ho |
| D862,716 S | 10/2019 | Cryan et al. |
| D865,986 S | 11/2019 | Cryan et al. |
| D879,983 S | 3/2020 | Wang |
| 10,940,311 B2 | 3/2021 | Gozani et al. |
| 11,058,877 B2 * | 7/2021 | Gozani ............... A61N 1/0456 |
| 11,247,040 B2 | 2/2022 | Ferree et al. |
| 2002/0010497 A1 | 1/2002 | Merfeld et al. |
| 2003/0023192 A1 | 1/2003 | Foxlin |
| 2003/0074037 A1 | 4/2003 | Moore et al. |
| 2003/0114892 A1 | 6/2003 | Nathan et al. |
| 2003/0208246 A1 | 11/2003 | Kotlik et al. |
| 2004/0049241 A1 | 3/2004 | Campos |
| 2004/0122483 A1 | 6/2004 | Nathan et al. |
| 2004/0173220 A1 | 9/2004 | Harry et al. |
| 2005/0059903 A1 | 3/2005 | Izumi |
| 2005/0080463 A1 | 4/2005 | Stahmann et al. |
| 2005/0097970 A1 | 5/2005 | Nurse |
| 2005/0131317 A1 | 6/2005 | Oddsson et al. |
| 2005/0234525 A1 | 10/2005 | Phillips |
| 2005/0283204 A1 | 12/2005 | Buhlmann et al. |
| 2006/0052788 A1 | 3/2006 | Thelen et al. |
| 2006/0064037 A1 | 3/2006 | Shalon et al. |
| 2006/0085047 A1 | 4/2006 | Unsworth et al. |
| 2006/0085049 A1 | 4/2006 | Cory et al. |
| 2006/0089683 A1 | 4/2006 | Hagglof et al. |
| 2006/0095088 A1 | 5/2006 | De Ridder |
| 2006/0173507 A1 | 8/2006 | Mrva et al. |
| 2006/0190057 A1 | 8/2006 | Reese |
| 2006/0251334 A1 | 11/2006 | Oba et al. |
| 2007/0021786 A1 | 1/2007 | Paris et al. |
| 2007/0060922 A1 | 3/2007 | Dreyfuss |
| 2007/0203435 A1 | 8/2007 | Novak |
| 2007/0203547 A1 | 8/2007 | Costello et al. |
| 2007/0276449 A1 | 11/2007 | Gunter et al. |
| 2008/0009772 A1 | 1/2008 | Tyler et al. |
| 2008/0077192 A1 | 3/2008 | Harry et al. |
| 2008/0146980 A1 | 6/2008 | Rousso et al. |
| 2008/0147143 A1 | 6/2008 | Popovic et al. |
| 2008/0147146 A1 | 6/2008 | Wahlgren et al. |
| 2008/0172102 A1 | 7/2008 | Shalev |
| 2008/0312709 A1 | 12/2008 | Volpe et al. |
| 2009/0030476 A1 | 1/2009 | Hargrove |
| 2009/0076364 A1 | 3/2009 | Libbus et al. |
| 2009/0082829 A1 | 3/2009 | Panken et al. |
| 2009/0082831 A1 | 3/2009 | Paul et al. |
| 2009/0112214 A1 | 4/2009 | Philippon et al. |
| 2009/0131993 A1 | 5/2009 | Rousso et al. |
| 2009/0203972 A1 | 8/2009 | Heneghan et al. |
| 2009/0240303 A1 | 9/2009 | Wahlstrand et al. |
| 2009/0264789 A1 | 10/2009 | Molnar et al. |
| 2009/0270947 A1 | 10/2009 | Stone et al. |
| 2009/0326604 A1 | 12/2009 | Tyler et al. |
| 2010/0004715 A1 | 1/2010 | Fahey |
| 2010/0010585 A1 | 1/2010 | Davis et al. |
| 2010/0042180 A1 | 2/2010 | Mueller et al. |
| 2010/0057149 A1 | 3/2010 | Fahey |
| 2010/0087903 A1 | 4/2010 | Van Herk et al. |
| 2010/0094103 A1 | 4/2010 | Kaplan et al. |
| 2010/0114257 A1 | 5/2010 | Torgerson |
| 2010/0131028 A1 | 5/2010 | Hsu et al. |
| 2010/0198124 A1 | 8/2010 | Bhugra |
| 2010/0217349 A1 | 8/2010 | Fahey |
| 2010/0241464 A1 | 9/2010 | Amigo et al. |
| 2010/0274304 A1 | 10/2010 | Wang et al. |
| 2011/0066209 A1 | 3/2011 | Bodlaender et al. |
| 2011/0106213 A1 | 5/2011 | Davis et al. |
| 2011/0166622 A1 | 7/2011 | Crosson et al. |
| 2011/0190594 A1 | 8/2011 | Heit et al. |
| 2011/0224665 A1 | 9/2011 | Crosby et al. |
| 2011/0245711 A1 | 10/2011 | Katra et al. |
| 2011/0257468 A1 | 10/2011 | Oser et al. |
| 2011/0264171 A1 | 10/2011 | Torgerson |
| 2011/0276107 A1 | 11/2011 | Simon et al. |
| 2011/0282164 A1 | 11/2011 | Yang et al. |
| 2012/0010680 A1 | 1/2012 | Wei et al. |
| 2012/0108998 A1 | 5/2012 | Molnar et al. |
| 2012/0123227 A1 | 5/2012 | Sun et al. |
| 2012/0130449 A1 | 5/2012 | Carlyon et al. |
| 2012/0303077 A1 | 11/2012 | De Vincentiis |
| 2012/0319816 A1 | 12/2012 | Al-Ali |
| 2013/0079846 A1 | 3/2013 | Single |
| 2013/0096641 A1 | 4/2013 | Strother et al. |
| 2013/0116514 A1 | 5/2013 | Kroner et al. |
| 2013/0158627 A1 | 6/2013 | Gozani et al. |
| 2013/0197341 A1 | 8/2013 | Grob et al. |
| 2013/0217998 A1 | 8/2013 | Mahfouz et al. |
| 2013/0317333 A1 | 11/2013 | Yang et al. |
| 2014/0005759 A1 | 1/2014 | Fahey et al. |
| 2014/0039450 A1 | 2/2014 | Green et al. |
| 2014/0057232 A1 | 2/2014 | Wetmore et al. |
| 2014/0081353 A1 | 3/2014 | Cook et al. |
| 2014/0088192 A1 | 3/2014 | Heller et al. |
| 2014/0107729 A1 | 4/2014 | Sumners et al. |
| 2014/0163444 A1 | 6/2014 | Ingvarsson et al. |
| 2014/0188194 A1 | 7/2014 | Schepis et al. |
| 2014/0206976 A1 | 7/2014 | Thompson et al. |
| 2014/0221797 A1 | 8/2014 | Bailey et al. |
| 2014/0245784 A1 | 9/2014 | Proud et al. |
| 2014/0245791 A1 | 9/2014 | Proud et al. |
| 2014/0276236 A1 | 9/2014 | Swain et al. |
| 2014/0276549 A1 | 9/2014 | Osorio |
| 2014/0296934 A1 | 10/2014 | Gozani et al. |
| 2014/0296935 A1 | 10/2014 | Ferree et al. |
| 2014/0309709 A1 | 10/2014 | Gozani et al. |
| 2014/0336725 A1 | 11/2014 | Nogueira |
| 2014/0336730 A1 | 11/2014 | Simon et al. |
| 2014/0343625 A1 | 11/2014 | O Laighin |
| 2014/0371547 A1 | 12/2014 | Gartenberg et al. |
| 2014/0371814 A1 | 12/2014 | Spizzirri et al. |
| 2014/0379045 A1 | 12/2014 | Rahimi et al. |
| 2015/0012068 A1 | 1/2015 | Bradley et al. |
| 2015/0045853 A1 | 2/2015 | Alataris et al. |
| 2015/0100107 A1 | 4/2015 | Kiani et al. |
| 2015/0157242 A1 | 6/2015 | Sabesan |
| 2015/0157868 A1 | 6/2015 | Franke et al. |
| 2015/0174402 A1 | 6/2015 | Thomas et al. |
| 2015/0238094 A1 | 8/2015 | Lai et al. |
| 2015/0272511 A1 | 10/2015 | Najafi et al. |
| 2015/0306387 A1 | 10/2015 | Kong et al. |
| 2015/0321000 A1 | 11/2015 | Rosenbluth et al. |
| 2015/0328467 A1 | 11/2015 | Demers et al. |
| 2015/0335288 A1 | 11/2015 | Toth et al. |
| 2015/0335877 A1 | 11/2015 | Jeffery et al. |
| 2016/0007931 A1 | 1/2016 | Rubin et al. |
| 2016/0029891 A1 | 2/2016 | Lin |
| 2016/0113551 A1 | 4/2016 | Annegam et al. |
| 2016/0144174 A1 | 5/2016 | Ferree et al. |
| 2016/0151628 A1 | 6/2016 | Simon et al. |
| 2016/0166198 A1 | 6/2016 | Oddsson et al. |
| 2016/0189371 A1 | 6/2016 | Krishna Rao et al. |
| 2016/0213924 A1 | 7/2016 | Coleman et al. |
| 2016/0235981 A1 | 8/2016 | Southwell et al. |

(56) References Cited

U.S. PATENT DOCUMENTS

| | | | |
|---|---|---|---|
| 2016/0242646 | A1 | 8/2016 | Obma |
| 2016/0243359 | A1 | 8/2016 | Sharma |
| 2016/0250464 | A1* | 9/2016 | Zschaeck .......... A61N 1/36036 607/62 |
| 2016/0310730 | A1 | 10/2016 | Martins et al. |
| 2016/0367823 | A1 | 12/2016 | Cowan et al. |
| 2017/0043160 | A1 | 2/2017 | Goodall et al. |
| 2017/0056650 | A1 | 3/2017 | Cohen et al. |
| 2017/0080207 | A1* | 3/2017 | Perez .................... A61F 5/0003 |
| 2017/0188864 | A1 | 7/2017 | Drury |
| 2017/0188872 | A1 | 7/2017 | Hughes et al. |
| 2017/0209693 | A1 | 7/2017 | An et al. |
| 2017/0224990 | A1 | 8/2017 | Goldwasser et al. |
| 2017/0238812 | A1 | 8/2017 | Atlas |
| 2017/0368345 | A1 | 12/2017 | Kong et al. |
| 2018/0000685 | A1 | 1/2018 | Maloney et al. |
| 2018/0028808 | A1 | 2/2018 | Ferree et al. |
| 2018/0132757 | A1* | 5/2018 | Kong .................... A61B 5/6885 |
| 2018/0177996 | A1 | 6/2018 | Gozani et al. |
| 2019/0001135 | A1 | 1/2019 | Yoo et al. |
| 2019/0022372 | A1 | 1/2019 | Dar et al. |
| 2019/0022386 | A1 | 1/2019 | Gozani et al. |
| 2019/0134393 | A1 | 5/2019 | Wong et al. |
| 2020/0179694 | A1 | 6/2020 | Kong et al. |
| 2020/0219615 | A1 | 7/2020 | Rabin et al. |
| 2021/0128904 | A1 | 5/2021 | Terekhov |
| 2021/0260374 | A1 | 8/2021 | Gozani et al. |

FOREIGN PATENT DOCUMENTS

| | | |
|---|---|---|
| CN | 1926496 | 3/2007 |
| CN | 101557788 | 10/2009 |
| CN | 101626804 | 1/2010 |
| CN | 102202131 | 9/2011 |
| CN | 102355847 | 2/2012 |
| CN | 102740919 | 10/2012 |
| DE | 102010052710 | 5/2012 |
| EP | 0 971 653 | 1/2000 |
| EP | 1 985 277 | 2/2015 |
| JP | 61-171943 | 10/1986 |
| JP | 4-347140 | 12/1992 |
| JP | 9-117453 | 5/1997 |
| JP | 2000-167067 | 6/2000 |
| JP | 2005-34402 | 2/2005 |
| JP | 2005-81068 | 3/2005 |
| JP | 2006-68300 | 3/2006 |
| JP | 4185846 | 9/2008 |
| WO | WO 97/42999 | 11/1997 |
| WO | WO 99/64105 | 12/1999 |
| WO | WO 03/051453 | 6/2003 |
| WO | WO 2004/078132 | 9/2004 |
| WO | WO 2007/061746 | 5/2007 |
| WO | WO 2008/079757 | 7/2008 |
| WO | WO 2008/088985 | 7/2008 |
| WO | WO 2009/036313 | 3/2009 |
| WO | WO 2011/075179 | 6/2011 |
| WO | WO 2011/137193 | 11/2011 |
| WO | WO 2012/116407 | 9/2012 |
| WO | WO 2013/028960 | 2/2013 |
| WO | WO 2014/172381 | 10/2014 |
| WO | WO 2015/123373 | 8/2015 |
| WO | WO 2016/201366 | 12/2016 |
| WO | WO 2018/089655 | 5/2018 |
| WO | WO 2020/033883 | 2/2020 |

OTHER PUBLICATIONS

Amazon, "Quell Wearable Pain Relief Technology Starter Kit", Oct. 18, 2017. http://www.amazon.com/Quell-Wearable-ReliefTechnology-Starter/dp/B075YVCLZT/ref=cm_cr_arp_d_product_top?ie=UTF8. Shown on p. 1. (Year: 2017).

Amft, O. et al., Sensing Muscle Activities with Body-Worn Sensors, Conference Paper, May 2006.

Ancoli-Israel, S. et al., The Role of Actigraphy in the Study of Sleep and Circadian Rhythms, Sleep, 2003, 26(3), p. 342-392.

Aurora, R. et al., The Treatment of Restless Legs Syndrome and Periodic Limb Movement Disorder in Adults—An Update for 2012: Practice Parameters with an Evidence-Based Systematic Review and Meta-Analyses, Sleep, 2012, vol. 35, No. 8, p. 1039-1062.

Barbarisi, Manlio et al., Pregabalin and Transcutaneous Electrical Nerve Stimulation for Postherpetic Neuralgia Treatment, The Clinical Journal of Pain, Sep. 2010;26(7):567-572.

Bifulco, P. et al., A Stretchable, Conductive Rubber Sensor to Detect Muscle Contraction for Prosthetic Hand Control, The 6th IEEE International Conference on E-Health and Bioengineering—EHB 2017, Jun. 22-24, 2017, pp. 173-176.

Bjordal JM et al., Transcutaneous electrical nerve stimulation (TENS) can reduce postoperative analgesic consumption. A meta-analysis with assessment of optimal treatment parameters for postoperative pain, European Journal of Pain, 2003, vol. 7(2): 181-188.

Bloodworth DM et al., Comparison of stochastic vs. conventional transcutaneous electrical stimulation for pain modulation in patients with electromyographically documented radiculopathy, American Journal of Physical Medicine & Rehabilitation, 2004, vol. 83(8): 584-591.

Bonnet, M. et al., Recording and Scoring Leg Movements, Sleep, 1993, vol. 16, No. 8, p. 748-759.

Boyle, J. et al., Randomized, Placebo-Controlled Comparison of Amitriptyline, Duloxetine, and Pregabalin in Patients With Chronic Diabetic Peripheral Neuropathic Pain, Diabetes Care, 2012, vol. 35, p. 2451-2458.

Chandran P et al., Development of opioid tolerance with repeated transcutaneous electrical nerve stimulation administration, Pain, 2003, vol. 102: 195-201.

Chen CC et al., A comparison of transcutaneous electrical nerve stimulation (TENS) at 3 and 80 pulses per second on cold-pressor pain in healthy human participants, Clinical Physiology and Functioning Imaging, 2010, vol. 30(4): 260-268.

Chen CC et al., An investigation into the effects of frequency-modulated transcutaneous electrical nerve stimulation (TENS) on experimentally-induced pressure pain in healthy human participants, The Journal of Pain, 2009, vol. 10(10): 1029-1037.

Chen CC et al., Differential frequency effects of strong nonpainful transcutaneous electrical nerve stimulation on experimentally induced ischemic pain in healthy human participants, The Clinical Journal of Pain, 2011, vol. 27(5): 434-441.

Chen CC et al., Does the pulse frequency of transcutaneous electrical nerve stimulation (TENS) influence hypoalgesia? A systematic review of studies using experimantal pain and healthy human participants, Physiotherapy, 2008, vol. 94: 11-20.

Claydon LS et al., Dose-specific effects of transcutaneous electrical nerve stimulation on experimental pain, Clinical Journal of Pain, 2011, vol. 27(7): 635-647.

Cole, R.J. et al., Automatic Sleep/Wake Identification From Wrist Activity, Sleep, 1992, 15(5), p. 461-469.

Cruccu G. et al., EFNS guidelines on neurostimulation therapy for neuropathic pain, European Journal of Neurology, 2007, vol. 14: 952-970.

Dailey DL et al., Transcutaneous Electrical Nerve Stimulation (TENS) Reduces Pain, Fatigue, and Hyperalgesia while Restoring Central Inhibition in Primary Fibromyalgia, Pain, Nov. 2013, vol. 154, No. 11, pp. 2554-2562.

Dailey, D. et al., Transcutaneous Electrical Nerve Stimulation Reduces Movement-Evoked Pain and Fatigue: A Randomized, Controlled Trial, Arthritis & Rheumatology, May 2020, vol. 72, No. 5, pp. 824-836.

Davies Hto et al., Diminishing returns or appropriate treatment strategy?—an analysis of short-term outcomes after pain clinic treatment, Pain, 1997, vol. 70: 203-208.

Desantana JM et al., Effectiveness of transcutaneous electrical nerve stimulation for treatment of hyperalgesia and pain, Curr Rheumatol Rep. 2008, vol. 10(6):492-499.

Dubinsky RM et al., Assessment: Efficacy of transcutaneous electric nerve stimulation in the treatment of pain in neurologic disorders (an evidence-based review): Report of the therapeutics and tech-

(56) References Cited

OTHER PUBLICATIONS nology assessment subcommittee of the american academy of neurology, Neurology, 2010, vol. 74: 173-176.

Fary RE et al., Monophasic electrical stimulation produces high rates of adverse skin reactions in healthy subjects, Physiotherapy Theory and Practice, 2011, vol. 27(3): 246-251.

Fishbain, David A. et al. Does Pain Mediate the Pain Interference with Sleep Problem in Chronic Pain? Findings from Studies for Management of Diabetic Peripheral Neuropathic Pain with Duloxetine, Journal of Pain Symptom Management, Dec. 2008; 36(6):639-647.

Fishbain, David A. et al., Transcutaneous Electrical Nerve Stimulation (TENS) Treatment Outcome in Long-Term Users, The Clinical Journal of Pain, Sep. 1996; 12(3):201-214.

Food and Drug Administration, Draft Guidance for Industry and Staff: Class II Special Controls Guidance Document: Transcutaneous Electrical Nerve Stimulator for Pain Relief, Apr. 5, 2010.

Garrison DW et al., Decreased activity of spontaneous and noxiously evoked dorsal horn cells during transcutaneous electrical nerve stimulation (TENS), Pain, 1994, vol. 58: 309-315.

Gilron, I. et al., Chronobiological Characteristics of Neuropathic Pain: Clinical Predictors of Diurnal Pain Rhythmicity, The Clinical Journal Of Pain, 2013.

Gozani SN et al., Fixed-Site High-Frequency Transcutaneous Electrical Nerve Stimulation for Treatment of Chronic Low Back and Lower Extremity Pain, Journal of Pain Research, 2016, vol. 9, pp. 469-479.

Hausdorff, J.M. et al., Gait Variability and Fall Risk in Community-Living Older Adults: A 1-Year Prospective Study, Arch Phys Med Rehabil, Aug. 2001, vol. 82, pp. 1050-1056.

Hori, T. et al., Skin Potential Activities And Their Regional Differences During Normal Sleep In Humans, The Japanese Journal of Physiology, 1970, vol. 20, p. 657-671.

Jelinek HF et al., Electric pulse frequency and magnitude of perceived sensation during electrocutaneous forearm stimulation, Arch Phys Med Rehabil, 2010, vol. 91: 1372-1382.

Jin DM et al., Effect of transcutaneous electrical nerve stimulation on symptomatic diabetic peripheral neuropathy: a meta-analysis of randomized controlled trials, Diabetes Research and Clinical Practice, 2010, vol. 89: 10-15.

Johnson MI et al., Analgesic effects of different frequencies of transcutaneous electrical nerve stimulation on cold-induced pain in normal subjects, Pain, 1989, vol. 39: 231-236.

Johnson MI et al., Transcutaneous Electrical Nerve Stimulation (TENS) and TENS-like devices: do they provide pain relief?, Pain Reviews, 2001, vol. 8: 7-44.

Johnson MI et al., Transcutaneous electrical nerve stimulation for the management of painful conditions: focus on neuropathic pain, Expert Review of Neurotherapeutics, 2011, vol. 11(5): 735-753.

Johnson, M.I. et al., An in-depth study of long-term users of transcutaneous electrical nerve stimulation (TENS). Implications for clinical use of TENS. Pain. Mar. 1991;44(3):221-229.

Kaczmarek, Kurt A. et al.. Electrotactile and Vibrotactile Displays for Sensory Substitution Systems. IEEE Trans. Biomed. Eng. Jan. 1991;38 (1):1-16.

Kantor G et al., The effects of selected stimulus waveforms on pulse and phase characteristics at sensory and motor thresholds, Physical Therapy, 1994, vol. 74(10): 951-962.

Keller, Thierry et al., Electrodes for transcutaneous (surface) electrical stimulation. J. Automatic Control, University of Belgrade. 2008; 18(2):35-45.

Koumans, A. J. R. et al., Electrodermal Levels And Fluctuations During Normal Sleep, Psychophysiology, 1968, 5(3), p. 300-306.

Kovacevic-Ristanovic, R. et al., Nonpharmacologic Treatment of Periodic Leg Movements in Sleep, Arch. Phys. Med. Rehabil., 1991, vol. 72, p. 385-389.

Kripke, D.F. et al., Wrist Actigraphic Scoring for Sleep Laboratory Patients: Algorithm Development, Journal of Sleep Research, 2010, 19(4), p. 612-619.

Law PPW et al., Optimal stimulation frequency of transcutaneous electrical nerve stimulation on people with knee osteoarthritis, J Rehabil Med, 2004, vol. 36: 220-225.

Leonard G et al., Deciphering the role of endogenous opioids in high-frequency TENS using low and high doses of naloxone, Pain, 2010, vol. 151: 215-219.

Levy et al., A comparison of two methods for measuring thermal thresholds in diabetic neuropathy, Journal of Neurology, Neurosurgery, and Psychiatry, 1989, vol. 52: 1072-1077.

Lopes, L. et al., Restless Legs Syndrome and Quality of Sleep in Type 2 Diabetes, Diabetes Care, 2005, vol. 28, No. 11, p. 2633-2636.

Lykken, D.T., Properties of Electrodes Used in Electrodermal Measurement. J. Comp. Physiol. Psychol. Oct. 1959; 52:629-634.

Lykken, D.T., Square-Wave Analysis of Skin Impedance. Psychophysiology. Sep. 1970; 7(2):262-275.

Macfarlane, T. et al., Whether the weather influences pain? Results from EpiFunD study in North West England, Rheumatology, 2010, vol. 49, pp. 1513-1520.

Melzack R et al., Pain mechanisms: A New Theory, Science, 1965, vol. 150(3699): 971-979.

Moran F et al., Hypoalgesia in response to transcutaneous electrical nerve stimulation (TENS) depends on stimulation intensity, The Journal of Pain, 2011, vol. 12(8): 929-935.

Nightingale, S., The neuropathic pain market, Nature Reviews, 2012, vol. 11, p. 101-102.

Okamoto-Mizuno. K. et al., Effects of thermal environment on sleep and circadlan rhythm, Journal of Physiological Anthropology, 2012, vol. 31, No. 14, pp. 1-9.

Oosterhof, Jan et al., Outcome of transcutaneous electrical nerve stimulation in chronic pain: short-term results of a double-blind, randomised, placebo-controlled trial. J. Headache Pain. Sep. 2006; 7 (4):196-205.

Oosterhof, Jan et al., The long-term outcome of transcutaneous electrical nerve stimulation in the treatment for patients with chronic pain: a randomized, placebo-controlled trial. Pain Pract. Sep. 2012; 12(7):513-522.

Ossipov MH et al., Central Modulation of Pain, The Journal of Clinical Investigation, Nov. 2010, vol. 120, No. 11, pp. 3779-3787.

Pantaleao MA et al., Adjusting pulse amplitude during transcutaneous electrical nerve stimulation (TENS) application produces greater hypoalgesia, The Journal of Pain, 2011, vol. 12(5): 581-590.

Paquet, J. et al., Wake Detection Capacity of Actigraphy During Sleep, Sleep, 2007, 30(10), p. 1362-1369.

Pieber K et al., Electrotherapy for the treatment of painful diabetic peripheral neuropathy: a review, Journal of Rehabilitation Medicine, 2010, vol. 42: 289-295.

Raskin, J. et al., A Double-Blind, Randomized Multicenter Trial Comparing Duloxetine with Placebo in the Management of Diabetic Peripheral Neuropathic Pain, Pain Medicine, 2005, 6(5), p. 346-356.

Sadeh, A., The Role and Validity of Actigraphy in Sleep Medicine: An Update, Sleep Medicine Reviews, 2011, vol. 15, p. 259-267.

Sadosky, A. et al., Burden of Illness Associated with Painful Diabetic Peripheral Neuropathy Among Adults Seeking Treatment in the US: Results from a Retrospective Chart Review and Cross-Sectional Survey, Diabetes, Metabolic Syndrome and Obesity: Targets and Therapy, 2013, vol. 6, p. 79-92.

Sano, A et al, Quantitative analysis of wrist electrodermal activity during sleep, International Journal of Psychophysiology, 2014, vol. 94, pp. 382-389.

Scherder, E. J. A. et al., Transcutaneous Electrical Nerve Stimulation (TENS) Improves the Rest-Activity Rhythm in Midstage Alzheimer's Disease, Behavioral Brain Research, 1999, vol. 101, p. 105-107.

Sheridan et al., Some Factors Influencing the Threshold of the Electrocutaneous Stimulus, Perceptual and Motor Skills, 1966, vol. 22, pp. 647-654.

Susi et al., Motion Mode Recognition and Step Detection Algorithms for Mobile Phone Users, Sensors, Jan. 24, 2013, vol. 13, pp. 1539-1562.

Taborri et al., A Novel HMM Distributed Classifier for the Detection of Gait Phases by Means of a Wearable Inertial Sensor Network, Sensors, Sep. 2014, vol. 14, pp. 16212-16234.

(56) References Cited

OTHER PUBLICATIONS

Timmermans, E. et al., Self-perceived weather sensitivity and joint pain in older people with osteoarthritis in six European countries: results from the European Project on OSteoArthritis (EPOSA), BMC Musculoskeletal Disorders, 2014, vol. 15, No. 66, pp. 1-11.
Tryon, W. W., Issues of Validity in Actigraphic Sleep Assessment, Sleep, 2004, 27(1), p. 158-165.
Tsai, Y. et al., Impact of Subjective Sleep Quality on Glycemic Control in Type 2 Diabetes Mellitus, Family Practice, 2012, vol. 29, p. 30-35.
Van Boxtel, A., Skin resistance during square-wave electrical pulses of 1 to 10 mA. Med. Biol. Eng. Comput. Nov. 1977; 15(6):679-687.
Van Someren, E. J. W. et al., Gravitational Artefact in Frequency Spectra of Movement Acceleration: Implications for Actigraphy in Young and Elderly Subjects, Journal of Neuroscience Methods, 1996, vol. 65, p. 55-62.
Waeber, R. et al., Biosection Search with Noisy Responses, SIAM J. Control Optim., 2013, vol. 51, No. 3, pp. 2261-2279.
Webster, J. B. et al., An Activity-Based Sleep Monitor System for Ambulatory Use, Sleep, 1982, 5(4), p. 389-399.
Zelman, D. C. et al., Sleep Impairment in Patients With Painful Diabetic Peripheral Neuropathy, The Clinical Journal Of Pain, 2006, 22(8), p. 681-685.
Zucconi, M. et al., The official World Association of Sleep Medicine (WASM) standards for recording and scoring periodic leg movements in sleep (PLMS) and wakefulness (PLMW) developed in collaboration with a task force from the International Restless Legs Syndrome Study Group (IRLSSG), Sleep Medicine, 2006, vol. 7, p. 175-183.
Vance et al., Using TENS for pain control: the state of the evidence, Pain Management, 2014, vol. 4, No. 3, pp. 197-209.
Mallik et al., Nerve Conduction Studies: Essentials and Pitfalls in Practice, Neurol Neurosurg Psychiatry, 2005, ii23-ii31.

\* cited by examiner

APPARATUS AND METHOD FOR THE AUTOMATED CONTROL OF TRANSCUTANEOUS ELECTRICAL NERVE STIMULATION BASED ON CURRENT AND FORECASTED WEATHER CONDITIONS

REFERENCE TO PENDING PRIOR PATENT APPLICATIONS

This patent application is a continuation of prior U.S. patent application Ser. No. 15/990,994, filed May 29, 2018 by Neurometrix, Inc for APPARATUS AND METHOD FOR THE AUTOMATED CONTROL OF TRANSCUTANEOUS ELECTRICAL NERVE STIMULATION BASED ON CURRENT AND FORECASTED WEATHER CONDITIONS, which patent application claims benefit of prior U.S. Provisional Patent Application Ser. No. 62/512,250, filed May 30, 2017 by NeuroMetrix, Inc. and Shai N. Gozani for AUTOMATED CONTROL OF TRANSCUTANEOUS ELECTRICAL NERVE STIMULATION BASED ON WEATHER PATTERNS The two (2) above-identified patent applications are hereby incorporated herein by reference.

FIELD OF THE INVENTION

This invention generally relates to Transcutaneous Electrical Nerve Stimulation (TENS) devices that deliver electrical currents across the intact skin of a user in order to provide symptomatic relief of chronic pain, and more particularly to TENS devices configured for the automated control of TENS therapy based on current and forecasted weather conditions, including the particular weather sensitivity of the user, in order to optimize pain relief.

BACKGROUND OF THE INVENTION

Transcutaneous electrical nerve stimulation (TENS) is the delivery of electricity (i.e., electrical stimulation) across the intact surface of a user's skin in order to activate sensory nerve fibers. The most common application of TENS therapy is to provide analgesia, such as for chronic pain. Other applications of TENS therapy include, but are not limited to, reducing the symptoms of restless leg syndrome, decreasing nocturnal muscle cramps, and providing relief from generalized pruritis. A conceptual model for how sensory nerve stimulation leads to pain relief was proposed by Melzack and Wall in 1965. Their theory stipulates that activation of sensory nerves (Aβ fibers) closes a "pain gate" in the spinal cord that inhibits the transmission of pain signals carried by nociceptive afferents (C and Aδ fibers) to the brain. In the past 20 years, anatomic pathways and molecular mechanisms that may underlie the pain gate have been identified. Sensory nerve stimulation (e.g., via TENS) activates the descending pain inhibition system, primarily the periaqueductal gray (PAG) and rostroventral medial medulla (RVM) located in the midbrain and medulla sections of the brainstem, respectively. The PAG has neural projections to the RVM, which in turn has diffuse bilateral projections into the spinal cord dorsal horn that inhibit ascending pain signal transmission.

TENS is typically delivered in short discrete pulses (with each pulse typically being several hundred microseconds in duration) at frequencies between about 10 and 150 Hz, through hydrogel electrodes placed on the user's body. TENS is characterized by a number of electrical parameters including the amplitude and shape of the stimulation pulse (which combine to establish the pulse charge), the frequency and pattern of the pulses, the duration of a therapy session and the interval between therapy sessions. All of these parameters are correlated to the therapeutic dose. For example, higher amplitude and longer pulses (i.e., larger pulse charge) increase the dose, whereas shorter therapy sessions decrease the dose. Clinical studies suggest that pulse charge and therapy session duration have the greatest impact on therapeutic dose.

To achieve maximum pain relief (i.e., hypoalgesia), TENS needs to be delivered at an adequate stimulation intensity. Intensities below the threshold of sensation are not clinically effective. The optimal therapeutic intensity is often described as one that is "strong yet comfortable". Most TENS devices rely on the user to set the stimulation intensity, usually through a manual intensity control comprising an analog intensity knob or digital intensity control pushbuttons. In either case (i.e., analog control or digital control), the user must manually increase the intensity of the stimulation to what the user believes to be a therapeutic level. Therefore, a major limitation of current TENS devices is that it may be difficult for many users to determine an appropriate therapeutic stimulation intensity. As a result, the user will either require substantial support from medical staff or they may fail to get pain relief due to an inadequate stimulation level.

A newly-developed wearable TENS device (Quell®, Neurometrix, Inc., Waltham, MA, USA) uses a novel method for calibrating the stimulation intensity in order to maximize the probability that the TENS stimulation intensity will fall within the therapeutic range. With the Quell® device, the user identifies their electrotactile sensation threshold and then the therapeutic intensity is automatically estimated by the TENS device based on the identified electrotactile sensation threshold.

Pain relief from TENS stimulation usually begins within 15 minutes of the stimulation onset and may last up to an hour following the completion of the stimulation period (also known as a "therapy session"). Each therapy session typically runs for 30-60 minutes. To maintain pain relief (i.e., hypoalgesia), TENS therapy sessions typically need to be initiated at regular intervals. Newly-developed wearable TENS devices, such as the aforementioned Quell® device, provide the user with an option to automatically restart therapy sessions at pre-determined time intervals.

The persistent nature of chronic pain and the convenience of "wear-and-forget" TENS technology may lead some users to wear the TENS device daily for an extended period of time. To achieve maximum pain relief, TENS needs to be delivered at an adequate stimulation intensity level throughout the day and also at night (i.e., when the user is asleep). The optimal therapeutic stimulation intensity level varies from person to person, and depends upon the electrotactile threshold of each individual user. Once the optimal setting for the therapeutic stimulation intensity level is determined for a particular user, it remains fixed for that user for all subsequent TENS therapeutic sessions throughout the day.

However, all organisms have internal "clocks" that regulate normal biological processes and normal physiological function. The most important and well understood internal "clock" is the circadian rhythm. In the absence of external entrainment cues, the human circadian rhythm has a 20 to 28 hour cycle. The circadian oscillator is synchronized to the physical 24-hour day-night cycle by environmental signals such as light. Therefore, a single time-invariant TENS dose may not provide consistent pain relief throughout the day for a TENS user.

A growing recognition of the importance of the circadian rhythm, and other temporal fluctuations, in various diseases and the efficacy of their treatments has led to the concept of "chronotherapy," which is an attempt to design therapeutic approaches that account for the temporal properties of human physiological function. By way of example but not limitation, circadian rhythms influence chronic pain and may impact the treatment of pain using TENS therapy. Variations in pain intensity over the course of the day are common. Some pain conditions, such as painful diabetic neuropathy, exhibit peak intensity (i.e., the greatest level of pain) in the evening, while other pain conditions, such as fibromyalgia, exhibit peak intensity (i.e., the greatest level of pain) in the morning. One significant implication of these fluctuations in the degree of pain experienced by the user over the course of the day is that a user may require a higher therapeutic dose (i.e., a higher level of TENS stimulation) at certain times of the day in order to achieve optimal and stable pain control.

A user's sensory threshold may vary over the course of the day, which may also impact the efficacy of TENS therapy at a given stimulation intensity level. In other words, the threshold at which a sensory stimulus (e.g., electrical stimulation, light, heat, etc.) is detected by the user is not constant, but varies over the course of the 24-hour cycle. Although, circadian variation in the perception threshold to electrical stimulation, commonly referred to as the "electrotactile threshold", has not been studied extensively, several published studies suggest that humans experience time-varying perception thresholds to electrical stimulation (e.g., TENS therapy). Most users experience their lowest perception threshold (i.e., greatest sensitivity) to electrical stimulation (e.g., TENS therapy) in the late afternoon and early evening (see, for example, Sheriden et al., "Some Factors Influencing the Threshold of the Electrocutaneous Stimulus". Percept. Mot. Skills, 1966). However, there is substantial inter-individual variation and some users experience a minimum perception threshold at other times of the day. The implication of a varying electrotactile perception threshold is that the therapeutic effect of TENS stimulation therapy may vary in a circadian fashion if the stimulation intensity is held constant throughout the day. More particularly, if the user's electrotactile perception threshold is low, then more sensory nerves will be stimulated as compared to when the user's electrotactile perception threshold is high.

The anatomical location where circadian modulation occurs may be in the periphery of the user's body, in the user's central nervous system (CNS), or both. In the periphery of the user's body, modulation of nerve stimulation may be due to changes in body surface temperature, biophysical changes in peripheral nerve membranes, and other effects. Circadian rhythms may also modulate sensory perception in the CNS where the integration of peripheral sensory signals may be amplified or attenuated in a time-varying fashion. Regardless of the site(s) of circadian control/modulation of the electrotactile perception threshold, the net effect is that the sensory input that triggers the descending pain inhibition system fluctuates in a rhythmic fashion, leading to an oscillation in the effective stimulation intensity. To maintain stable and uniform therapeutic effectiveness of TENS therapy for a particular user, the circadian rhythms of that particular user can be exploited in order to optimally regulate TENS stimulation parameters, with the goal of enhancing TENS therapeutic effectiveness by counteracting the time-dependent nature of the sensory perception threshold and pain level.

In addition to the foregoing, people with chronic pain frequently report that the weather influences their pain. In some cases, pain fluctuates concurrently with the weather and/or other environmental factors. For example, it is common to hear people complain of more pain in cold weather. In other cases, changes in the weather appear to influence pain more than the actual current weather conditions. Various aspects of weather have been shown to impact pain, including temperature, humidity, barometric pressure, wind, and precipitation. In a population study of 2491 subjects, a strong relationship was observed for the sub-group characterized by chronic widespread pain between lack of sunshine, lower temperatures, and pain reporting (Macfarlane T V et al, Whether the weather influences pain? Results from the EpiFunD study in North West England, Rheumatology 2010; 49:1513-1520). In another study, weather sensitivity was reported by a majority (66%) of 712 study participants with osteoarthritis, particularly among women and more anxious people (Timmermans E J et al, Self-perceived Weather Sensitivity and Joint Pain in Older People with Osteoarthritis in Six European Countries: Results from the European Project on OSteoArthritis (EPOSA). BMC Musculoskeletal Disorders 2014, 15:66). Staying active, and regular exercise, reduce chronic pain severity, and weather elements could negatively affect activity levels (and hence pain levels). For example, inclement weather may keep chronic pain suffers indoors, preventing them from carrying out their regular exercise routines (e.g., walking outside).

While not every chronic pain sufferer may be impacted by changes in weather conditions and/or environmental factors, many chronic pain sufferers do report an impact of certain changes in weather conditions on their pain perception. Indeed, about 50% of users of a commercially-available TENS device who reported on their chronic condition said "yes" to the question "Does weather affect your chronic pain?". With weather conditions and weather forecasts readily available via mobile apps on connected devices (e.g., smartphones), it would be beneficial to provide a novel TENS device that can leverage the current and forecasted weather conditions by automatically adjusting the pain-relieving therapy schedules of the TENS device so as to minimize the impact of weather on perceived pain for those TENS users with weather sensitivity.

SUMMARY OF THE INVENTION

The present invention comprises the provision and use of a novel TENS device which comprises a stimulator designed to be placed on a user's upper calf (or other anatomical location) and a pre-configured electrode array designed to provide electrical stimulation to at least one nerve disposed in the user's upper calf (or other anatomical location). A significant feature of the present invention is that the novel TENS device automatically adjusts the TENS stimulation parameters according to the current and forecasted weather conditions so as to optimize the TENS therapy dose for pain relief without requiring direct intervention of the user.

In one preferred form of the present invention, there is provided apparatus for transcutaneous electrical nerve stimulation in a user, the apparatus comprising:
    a stimulator for electrically stimulating at least one nerve with at least one stimulation pulse;
    a controller connected to said stimulator for controlling at least one characteristic of said at least one stimulation pulse;

an analyzer for identifying the current and future presence of pain-altering patterns based on weather and/or environmental factors; and a processor connected to said analyzer and said controller for modulating said at least one characteristic of said at least one stimulation pulse according to said pain-altering patterns identified by said analyzer.

In another preferred form of the present invention, there is provided a method for controlling transcutaneous electrical nerve stimulation based on weather and/or environmental patterns, said method comprising the steps of:

providing apparatus for transcutaneous electrical nerve stimulation in a user, said apparatus comprising:
    a stimulator for electrically stimulating at least one nerve with at least one stimulation pulse;
    a controller connected to said stimulator for controlling at least one characteristic of said at least one stimulation pulse; and
    a processor connected to said controller for modulating said at least one characteristic of said at least one stimulation pulse;

determining the current and future presence of pain-altering patterns based on weather and/or environmental factors;

using said stimulator to electrically stimulate at least one nerve, including modulating said at least one characteristic of said at least one stimulation pulse according to presence and timing of said pain-altering patterns based on weather and/or environment factors.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

The present invention comprises the provision and use of a novel TENS device which comprises a stimulator designed to be placed on a user's upper calf (or other anatomical location) and a pre-configured electrode array designed to provide electrical stimulation to at least one nerve disposed in the user's upper calf (or other anatomical location). In one form of the invention, there is provided a novel TENS device which automatically adjusts stimulation parameters according to the time of day. In another form of the invention, there is provided a novel TENS device which automatically adjusts stimulation parameters based on current and forecasted weather conditions and/or environmental factors to optimize the TENS therapy dose for pain relief without direct intervention of the user.

The TENS Device in General

Figure 1:
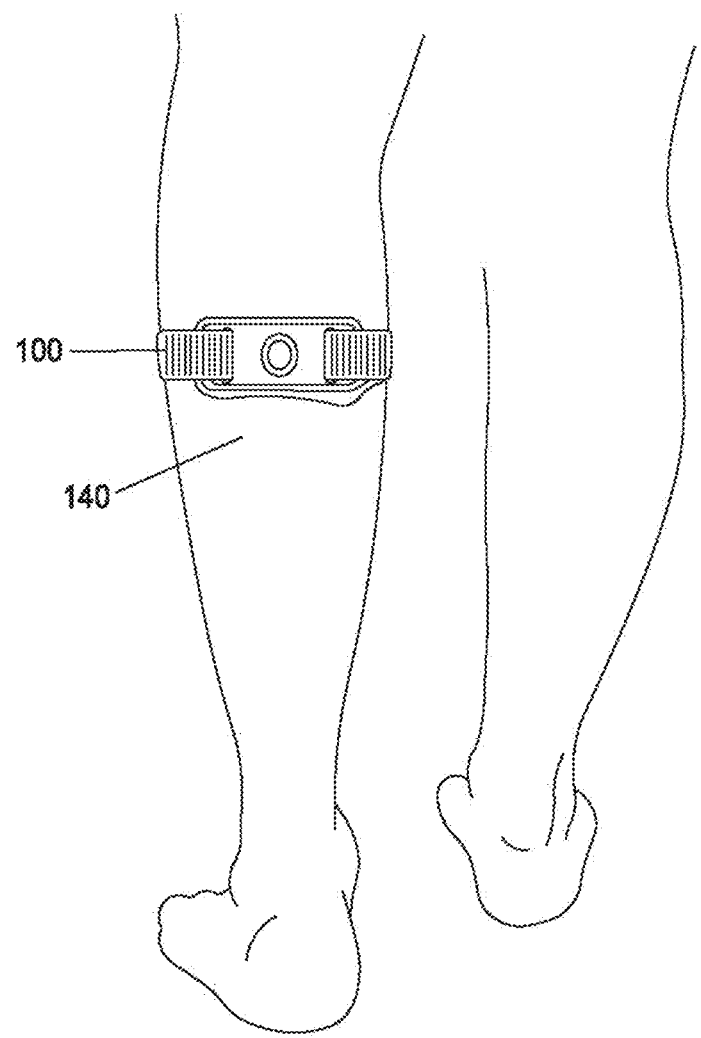
FIG. 1 is a schematic view showing a novel TENS device formed in accordance with the present invention, wherein the novel TENS device is mounted to the upper calf of a user.

More particularly, and looking now at FIG. 1, there is shown a novel TENS device 100 formed in accordance with the present invention, with novel TENS device 100 being shown worn on a user's upper calf 140. A user may wear TENS device 100 on one leg or on both legs (either one at a time or simultaneously) or a user may wear a TENS device 100 on another area of the body, separate from, or in addition to, a TENS device worn on one leg (or both legs) of the user.

Figure 2:
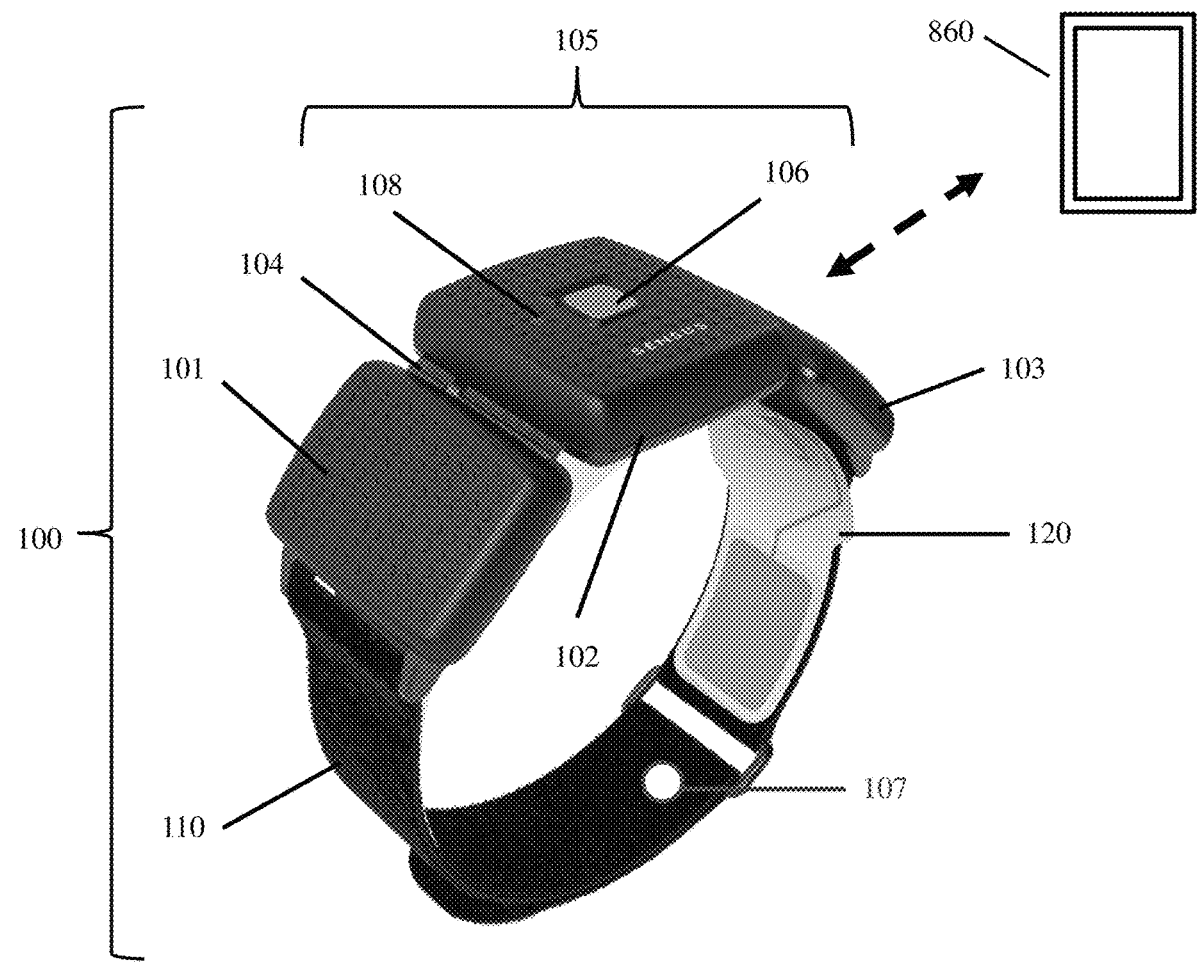
FIG. 2 is a schematic view showing the novel TENS device of FIG. 1 in greater detail.

Looking next at FIG. 2, TENS device 100 is shown in greater detail. TENS device 100 preferably comprises three primary components: a stimulator 105, a strap 110, and an electrode array 120 (comprising a cathode electrode and an anode electrode appropriately connected to stimulator 105 as is well known in the art). As shown in FIG. 2, stimulator 105 generally comprises three mechanically and electrically inter-connected compartments 101, 102, and 103. Compartments 101, 102, 103 are preferably inter-connected by hinge mechanisms 104 (only one of which is visible in FIG. 2), thereby allowing TENS device 100 to conform to the curved anatomy of a user's leg. In a preferred embodiment of the present invention, compartment 102 houses the TENS stimulation circuitry (except for a battery) and user interface elements 106 and 108. Compartment 102 also houses an accelerometer 172 (see FIG. 4), preferably in the form of a MEMS digital accelerometer microchip (e.g., Freescale MMA8451Q), for detecting user gestures such as taps to the central compartment 102, user leg and body orientation, and user leg and body motion. Compartment 102 also houses a real-time clock 505 (FIG. 4) and a temperature sensor 107 (FIG. 4) for measuring the user's skin surface temperature. In one preferred form of the present invention, compartments 101 and 103 are smaller, auxiliary compartments that house a battery for powering the TENS stimulation circuitry and other circuitry, and other ancillary elements, such as an ambient light sensor or detector 510 (FIG. 4) for determining ambient light conditions, and a wireless interface unit (not shown) of the sort well known in the art for allowing TENS device 100 to wirelessly communicate with other elements (e.g., a hand-held electronic device such as a smartphone 860). In another form of the present invention, only one or two compartments may be used for housing all the TENS stimulation circuitry, battery, and other ancillary elements of the present invention. In another form of the present invention, a greater number of compartments are used, e.g., to conform better to the body and to improve user comfort. And in still another form of the present invention, a flexible circuit board is used to distribute the TENS stimulation circuitry and other circuitry more evenly around the leg and thereby reduce thickness.

As discussed above, temperature sensor 107 is preferably disposed within compartment 102 of stimulator 105. However, it should be appreciated that, if desired, temperature sensor 107 may be embedded in the strap 110 (e.g., in the manner shown in FIG. 2) in order to measure the user's skin temperature, with the temperature measurement being electrically communicated to stimulator 105 (e.g., wirelessly or via a lead embedded in strap 110, not shown).

Still looking at FIG. 2, interface element 106 preferably comprises a push button for user control of electrical stimulation by TENS device 100, and interface element 108 preferably comprises an LED for indicating stimulation status and providing other feedback to the user. Although a single LED is shown, interface element 108 may comprise multiple LEDs with different colors. Additional user interface elements (e.g., an LCD display, audio feedback through a beeper or voice output, haptic devices such as a vibrating element, a smartphone running an appropriate app, etc.) are also contemplated and are within the scope of the present invention.

In one preferred form of the invention, TENS device 100 is configured to be worn on the user's upper calf 140 as shown in FIG. 1 (although it should be appreciated that TENS device 100 may be worn on other anatomical locations or multiple TENS devices 100 may be worn on various anatomical locations, etc.). TENS device 100 (comprising stimulator 105, electrode array 120, and strap 110) is secured to upper calf 140 (or other anatomical location) of the user by placing the apparatus in position and then tightening strap 110. More particularly, in one preferred form of the invention, electrode array 120 is deliberately sized and configured so that it will apply appropriate electrical stimulation to the appropriate anatomy of the user regardless of the specific rotational position of TENS device 100 on the leg (or other anatomical location) of the user. Although the preferred embodiment of the present invention comprises placement of the TENS device on the upper calf of the user, additional locations (such as above the knee, on an upper extremity, etc.) are also contemplated and considered to be within the scope of the present invention. Furthermore, it is also contemplated that the TENS device may be placed on other anatomical locations of the user, e.g., the lower back of the user (however, it will be appreciated that in some of these alternative anatomical locations, electrode array 120 may not be able to supply appropriate electrical stimulation to the appropriate anatomy of the user regardless of the specific rotational position of the TENS device 100 on the anatomy of the user).

Figure 3:
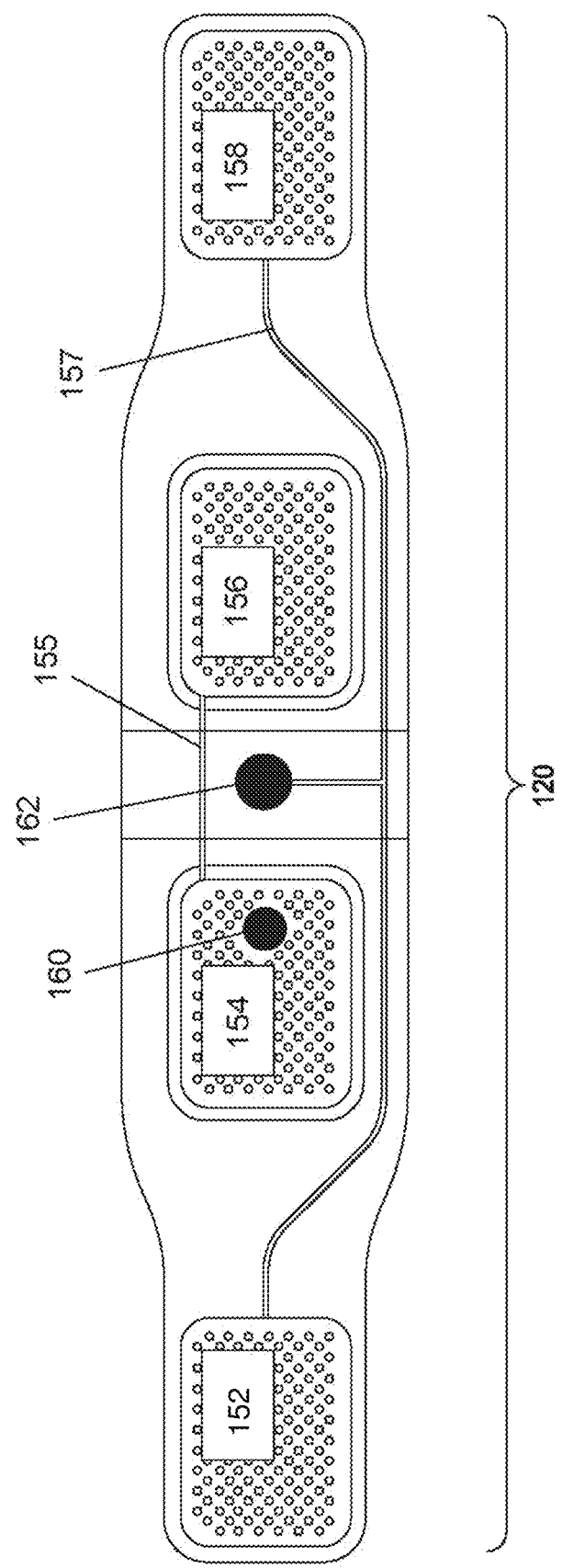
FIG. 3 is a schematic view showing the electrode array of the novel TENS device of FIGS. 1 and 2 in greater detail.

FIG. 3 shows a schematic view of one preferred embodiment of electrode array 120. Electrode array 120 preferably comprises four discrete electrodes 152, 154, 156, 158, each having an equal or similar size (i.e., an equal or similar size surface area). Electrodes 152, 154, 156, 158 are preferably connected in pairs so that electrodes 154 and 156 (representing the cathode of TENS device 100) are electrically connected to one another (e.g., via connector 155), and so that electrodes 152 and 158 (representing the anode of TENS device 100) are electrically connected to one another (e.g., via connector 157). It should be appreciated that electrodes 152, 154, 156, 158 are preferably appropriately sized, and connected in pairs, so as to ensure adequate skin coverage regardless of the rotational position of TENS device 100 (and hence regardless of the rotational position of electrode array 120) on the leg (or other anatomical location) of a user. Furthermore, it should be appreciated that electrodes 152, 154, 156, 158 are not connected in an interleaved fashion, but rather are connected so that the two inside electrodes 154, 156 are connected to one another, and so that the two outside electrodes 152, 158 are connected to one another. This electrode connection pattern ensures that if the two outer electrodes 152, 158 should inadvertently come into contact with one another, an electrical short of the stimulation current flowing directly from cathode to anode will not occur (i.e., the electrode connection pattern ensures that the therapeutic TENS current is always directed through the tissue of the user).

Figure 4:
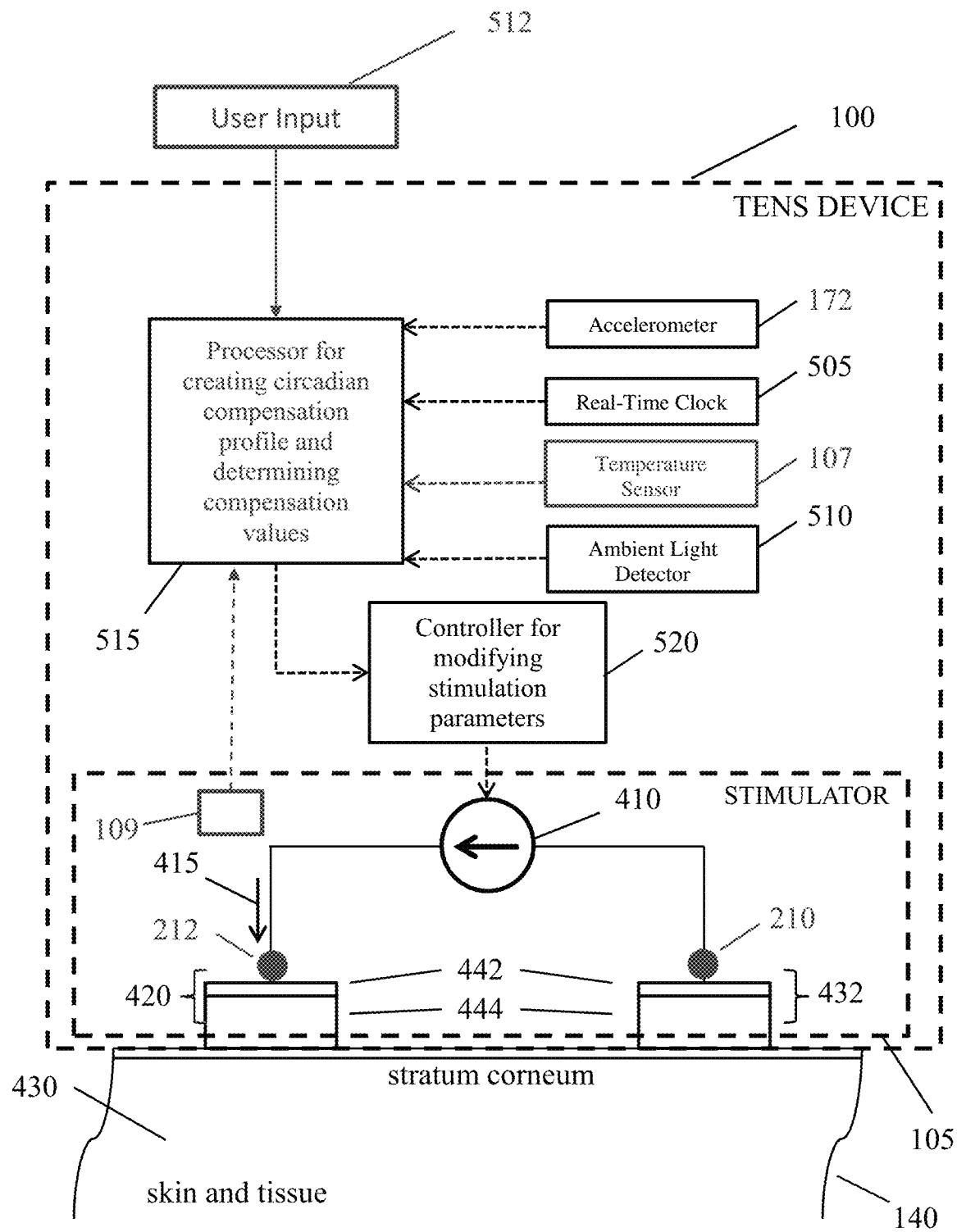
FIG. 4 is a schematic view of the novel TENS device of FIGS. 1-3, including its circadian compensation processor for creating compensation profiles and determining compensation values.

Electrical current (i.e., for therapeutic electrical stimulation to the tissue) is provided to the electrode pairs 154, 156 and 152, 158 by connectors 160, 162 which mate with complementary connectors 210, 212, respectively, on stimulator 105 (see FIG. 4). Stimulator 105 generates electrical currents that are passed through electrodes 154, 156 and electrodes 152, 158 via connectors 160, 162, respectively.

In one preferred embodiment of the present invention, the skin-contacting conductive material of electrodes 152, 154, 156, 158 is a hydrogel material which is "built into" electrodes 152, 154, 156, 158. The function of the hydrogel material on the electrodes is to serve as an interface between the electrodes 152, 154, 156, 158 and the skin of the user (i.e., within, or adjacent to, or proximal to, the portion of the user's body in which the sensory nerves which are to be stimulated reside). Other types of electrodes such as dry electrodes and non-contact stimulation electrodes have also been contemplated.

FIG. 4 is a schematic representation of the current flow between TENS device 100 and the user. As seen schematically in FIG. 4, stimulation current 415 from a constant current source 410 flows into the user's tissue 430 (e.g., the user's upper calf) via an anode electrode 420 (which anode electrode 420 comprises the aforementioned electrodes 152, 158). Anode electrode 420 comprises a conductive backing (e.g., silver hatch) 442 and hydrogel 444. The current passes through the user's tissue 430 and returns to constant current source 410 through cathode electrode 432 (which cathode electrode 432 comprises the aforementioned electrodes 154, 156). Cathode electrode 432 also comprises a conductive backing 442 and hydrogel 444. Constant current source 410 preferably provides an appropriate biphasic waveform (i.e., biphasic stimulation pulses) of the sort well known in the art of TENS therapy. In this respect it should be appreciated that the designation of "anode" and "cathode" electrodes is purely notational in the context of a biphasic waveform (i.e., when the biphasic stimulation pulse reverses its polarity in its second phase of the biphasic TENS stimulation, current will be flowing into the user's body via "cathode" electrode 432 and out of the user's body via "anode" electrode 420).

Figure 5:
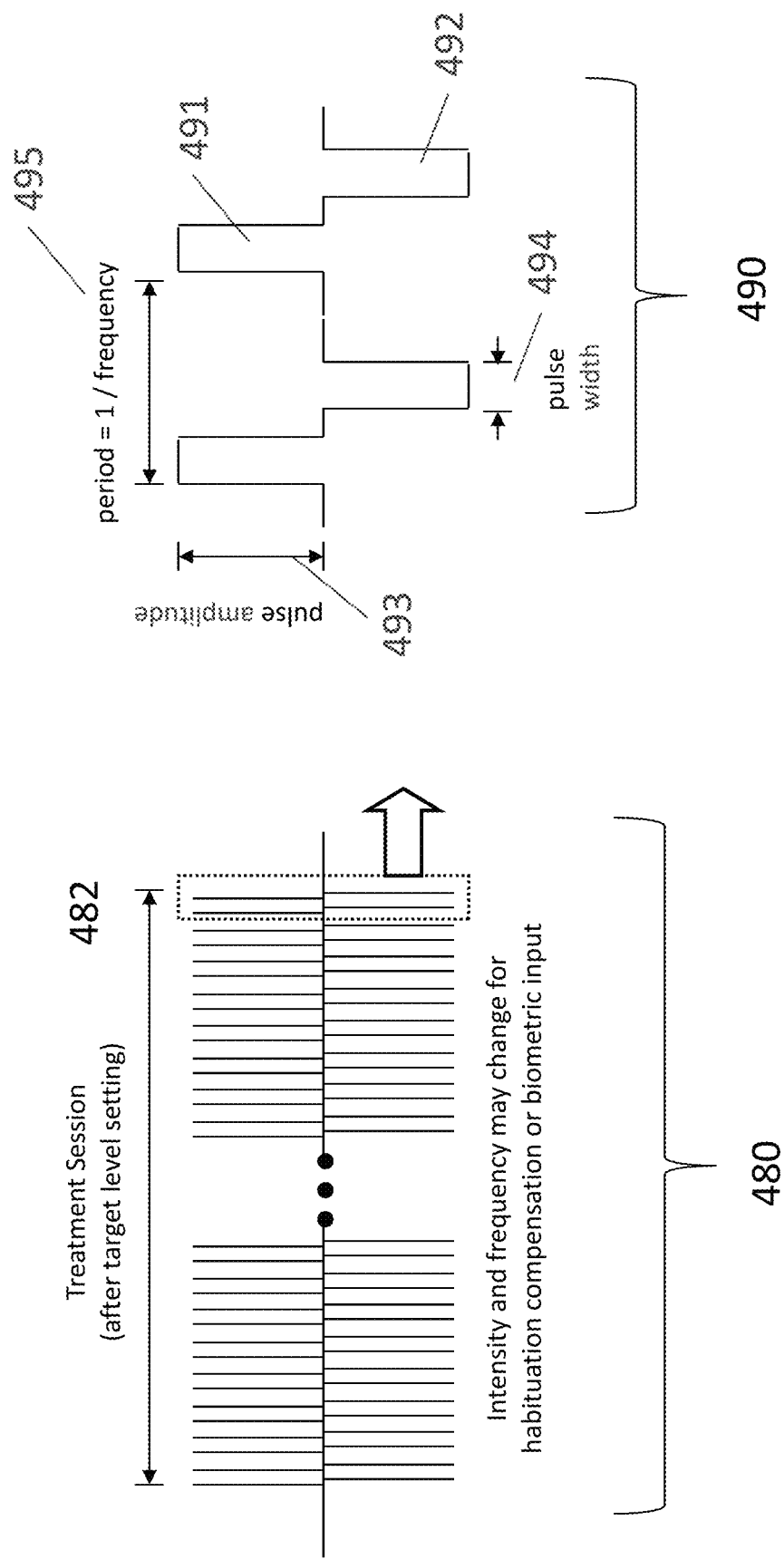
FIG. 5 is a schematic view showing the stimulation pulse train generated by the stimulator of the novel TENS device of FIGS. 1-4.

FIG. 5 is a schematic view showing a pulse train 480 provided by stimulator 105 during a TENS therapy session, and the waveform of two individual pulses 490. In one form of the invention, each pulse waveform is charge-balanced for two phases 491 and 492 of the pulse which prevents iontophoretic build-up under the electrodes of the electrode array 120 that can lead to skin irritation and potential skin damage. In another form of the invention, the individual pulses are unbalanced, however, charge-balancing is achieved across multiple consecutive pulses. Pulses of fixed or randomly varying frequencies persist throughout the duration of the therapy session 482. The intensity of the stimulation (i.e., the amplitude 493 of the current delivered by stimulator 105) is adjusted in response to user input and for habituation compensation, as will hereinafter be discussed in further detail.

In prior U.S. patent application Ser. No. 13/678,221, filed Nov. 15, 2012 by Neurometrix, Inc. and Shai N. Gozani et al. for APPARATUS AND METHOD FOR RELIEVING PAIN USING TRANSCUTANEOUS ELECTRICAL NERVE STIMULATION, issued as U.S. Pat. No. 8,948,876 on Feb. 3, 2015, which patent is hereby incorporated herein by reference, apparatus and methods are disclosed for allowing a user to personalize TENS therapy stimulation intensity according to the electrotactile perception threshold of the user at the time of the setup of the TENS device. U.S. Pat. No. 8,948,876 also discloses apparatus and methods to automatically restart additional therapy sessions after an initial manual start by the user. In prior U.S. patent application Ser. No. 14/230,648, filed Mar. 31, 2014 by NeuroMetrix, Inc. and Shai Gozani et al. for DETECTING CUTANEOUS ELECTRODE PEELING USING ELECTRODE-SKIN IMPEDANCE, issued as U.S. Pat. No. 9,474,898 on Oct. 25, 2016, which patent is hereby incorporated herein by reference, apparatus and methods are disclosed which allow safe delivery of TENS therapies at night when the user is asleep. These methods and apparatus allow the TENS device to be worn by a user for an extended period of time, including 24 hours a day.

A fixed TENS stimulation level may not be appropriate to deliver consistently comfortable and effective pain relief to a user throughout both the day and the night, since the impact of circadian or other time-varying rhythms mitigates the effectiveness of TENS stimulation. Parameters impacting TENS stimulation effectiveness include, but are not limited to, stimulation pulse amplitude 493 and pulse width 494, pulse frequency 495, and therapy session duration 482. By way of example but not limitation, higher amplitude and longer pulses (i.e., larger pulse charge) increase the stimulation delivered to the user (i.e., the stimulation "dose"), whereas shorter therapy sessions decrease stimulation delivered to the user (i.e., the stimulation "dose"). Clinical studies suggest that pulse charge (i.e., pulse amplitude and pulse width) and therapy session duration have the greatest impact on the therapeutic stimulation delivered to the user (i.e., the therapeutic stimulation "dose"). A therapy session is usually followed by a rest period before another therapy session is initiated. The ratio between therapy session duration and the time between the start of two consecutive therapy sessions is referred to as "therapy duty cycle".

Circadian Rhythm Compensation for TENS Therapy

Figure 6:
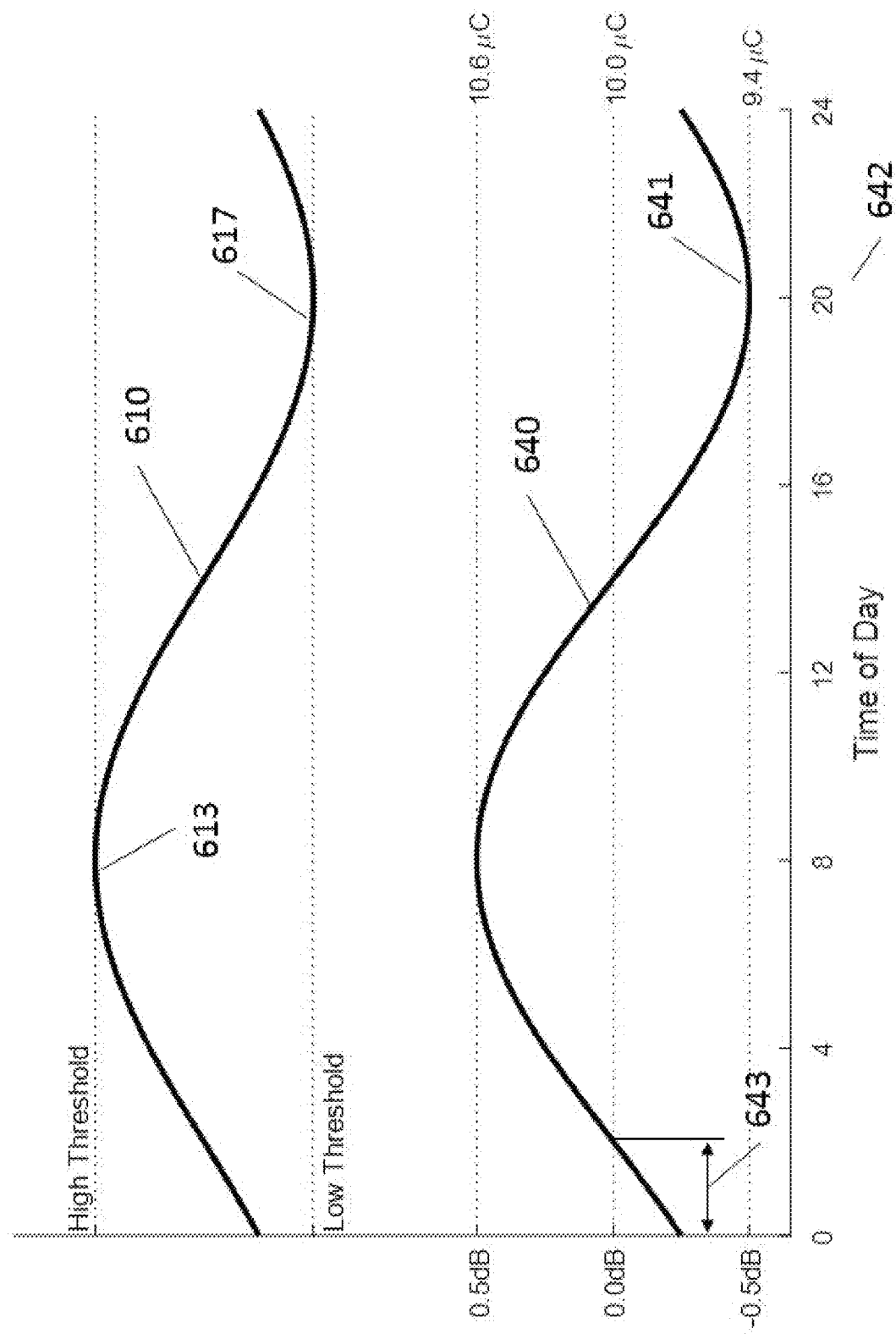
FIG. 6 is a schematic view showing exemplary circadian fluctuation in the electrotactile perception threshold and a matching circadian compensation function for regulating the stimulation pulse intensity delivered to a user by the novel TENS device of FIGS. 1-4.

One object of the present invention is to permit TENS device 100 to automatically offset the impact of circadian or other time-varying rhythms on the comfort and efficacy of TENS stimulation therapy, where efficacy is usually considered to be analgesia (i.e., the alleviation of pain) but may also be viewed more broadly in terms of other clinical effects of TENS such as, but not limited to, therapy for sleep disorders, therapy for muscle cramps, and therapy for treating pruritus. More particularly, the present invention automatically modulates at least one TENS stimulation parameter in order to compensate for the effect of at least one circadian rhythm. By way of example but not limitation, as previously discussed, it is known that an individual's electrotactile perception threshold varies over the course of a day in a circadian fashion. FIG. 6 shows an example of the circadian fluctuation in the electrotactile perception threshold 610 for an exemplary user over the course of a day. If constant electrical parameters are used throughout the day, then at times when the elecrotactile perception threshold is low (617), e.g., during the early evening, the user may perceive a strong and potentially uncomfortable electrical stimulation when stimulated by TENS device 100. Conversely, when the electrotactile perception threshold is high (613), e.g., during the morning, the user may perceive a weak and potentially therapeutically sub-optimal electrical stimulation. In order to avoid differences in user perception regarding stimulation intensity which can result from circadian fluctuation in the user's electrotactile perception threshold, in one preferred form of the present invention, TENS device 100 is configured to automatically adjust TENS stimulation parameters (e.g., pulse amplitude, pulse length, etc.) so that the user experiences consistently comfortable and therapeutically effective stimulation throughout the entire day. In another form of the invention, TENS device 100 is configured to automatically adjust TENS stimulation parameters (e.g., pulse amplitude, pulse length, etc.) in order to account for circadian fluctuations in the user's pain level. In another form of the invention, TENS device 100 is configured to provide adjusted TENS stimulation (i.e., by adjusting one or more TENS stimulation parameters) which is appropriate for a specific time of day, such as adjusting different stimulation parameters in the daytime periods and the nighttime periods.

In one preferred form of the present invention, the modulated stimulation parameters are pulse amplitude 493 and pulse width 494, or a combination of pulse amplitude 493 and pulse width 494 (pulse charge), since these stimulation parameters are known to have a direct impact on both comfort and analgesic efficacy. In another form of the invention, the modulated stimulation parameter is the pulse frequency 495. In yet another form of the invention, the modulated stimulation parameter is the duration of the therapy session 482. In another form of the invention, the modulated stimulation parameter is the elapsed time between consecutive therapy sessions. Modulation of other stimulation parameters, or combinations of stimulation parameters, falls within the scope of the present invention. By way of example but not limitation, in one form of the invention, the pulse charge and the pulse frequency are concurrently regulated in order to compensate for one or more circadian rhythms.

In one preferred form of the invention, the automatic compensation for temporal fluctuations (i.e., the automatic modulation of one or more stimulation parameters) is accomplished through a time-dependent function that offsets the actual stimulation intensity delivered to the user by TENS device 100. In the case of a circadian rhythm, this compensation is sometimes hereinafter called a circadian compensation function (CCF). The CCF modulates an electrical stimulation parameter during TENS therapy so as to offset the effect of a circadian rhythm on TENS therapy. In a preferred form of the invention, the stimulation parameter p(t) is modulated by a time-varying factor Δ(t), as described by Equation 1, $$\Delta(t)=A\sin(\omega t-\delta) \qquad \text{Eq. 1}$$

where ω is the angular frequency of the circadian rhythm. In the preferred embodiment, we assume that the user has a normal circadian rhythm that is entrained to the day night 24-hour cycle (86,400 seconds). Therefore, the angular frequency is 2π/86400 or 72.7×10$^{-6}$ radians (i.e., sec$^{-1}$). t is the time of day measured in seconds. δ is the phase delay in radians. A is the magnitude of the circadian compensation factor, usually represented in decibels. In a preferred form of the invention, the circadian compensation factor has a value of 0.5 dB, although values from 0.5 to 2 dB are common. If both p(t) and Δ(t) are expressed in decibels, then the modified time-varying electrical parameter $p_m(t)$ is given by Equation 2, $$p_m(t)=p(t)+\Delta(t) \qquad \text{Eq. 2.}$$

With A=0.5 dB, the CCF modulates the stimulation intensity by a multiplicative factor ranging from 0.94 to 1.06 (i.e., approximately ±6%). For example, if the purpose of the CCF is to regulate pulse charge with a baseline value of 10 μC, then the CCF will modulate the pulse charge from 9.4 μC to 10.6 μC depending on the time of day. δ is the phase delay of the circadian rhythm, measured in radians. FIG. 6 shows an example of a CCF 640 that offsets a circadian rhythm of the electrotactile perception threshold 610. In this example, the electroctactile perception threshold of the circadian rhythm has a minimum threshold 617 at time 642 (8 PM or Hour 20) and therefore the CCF 640 also has its minimum 641 at time 642 (8 PM or Hour 20). The phase delay δ 643 is 2π(2/24). There is no net effect on pulse charge over the course of a day.

An important assumption implicit in the CCF of Equation 1 is that the circadian rhythm follows a sinusoidal pattern. Circadian rhythms typically exhibit features of sinusoidal rhythms, repeatedly ascending to a maximum value, steadily decreasing to a minimum value and then increasing again. Therefore, mathematical models of circadian rhythms often utilize sine and cosine functions. This approach appears to provide a good fit to many types of circadian data such as core body temperature. In some instances, non-sinusoidal shapes such as square wave approximations better match the data. Although the preferred embodiment utilizes a sinusoidal function, alternative circadian rhythm models may be used and fall within the scope of the invention.

The CCF must be customized for each user. The most straightforward approach for customizing the CCF for each user is to ask the user what time of the day the uncompensated TENS stimulation feels strongest in the case of constructing a circadian rhythm of the electrotactial perception threshold. Similarly, a circadian rhythm for the pain intensity is constructed by identifying the time when is the pain level is the greatest. In one preferred embodiment, the CCF is then "shifted" in time to match the specified timing information provided by the user. Another approach to customize the CCF for individuals is to measure relevant physiological parameters such as skin temperature, skin impedance, and Galvanic skin response over the course of a day. Measurements from several days can also be used to calculate an average CCF (i.e., by using a processor included in TENS device 100 for creating a circadian compensation profile and determining compensation values, as will hereinafter be discussed in further detail). In another form of the invention, measured physiological values as a function of measurement time are used by the processor 515 to calculate the CCF. In yet another form of the invention, a suitable function with parametric model parameters is fitted to the measured values to calculate the CCF. And in another form of the invention, an initial CCF profile can be created based on demographic and physiological characteristics of the user, which may be used to calculate the CCF for a particular user. Subsequently manual adjustments of TENS stimulation parameters by the user can be used to refine the initial (i.e., calculated) CCF.

Figure 7:
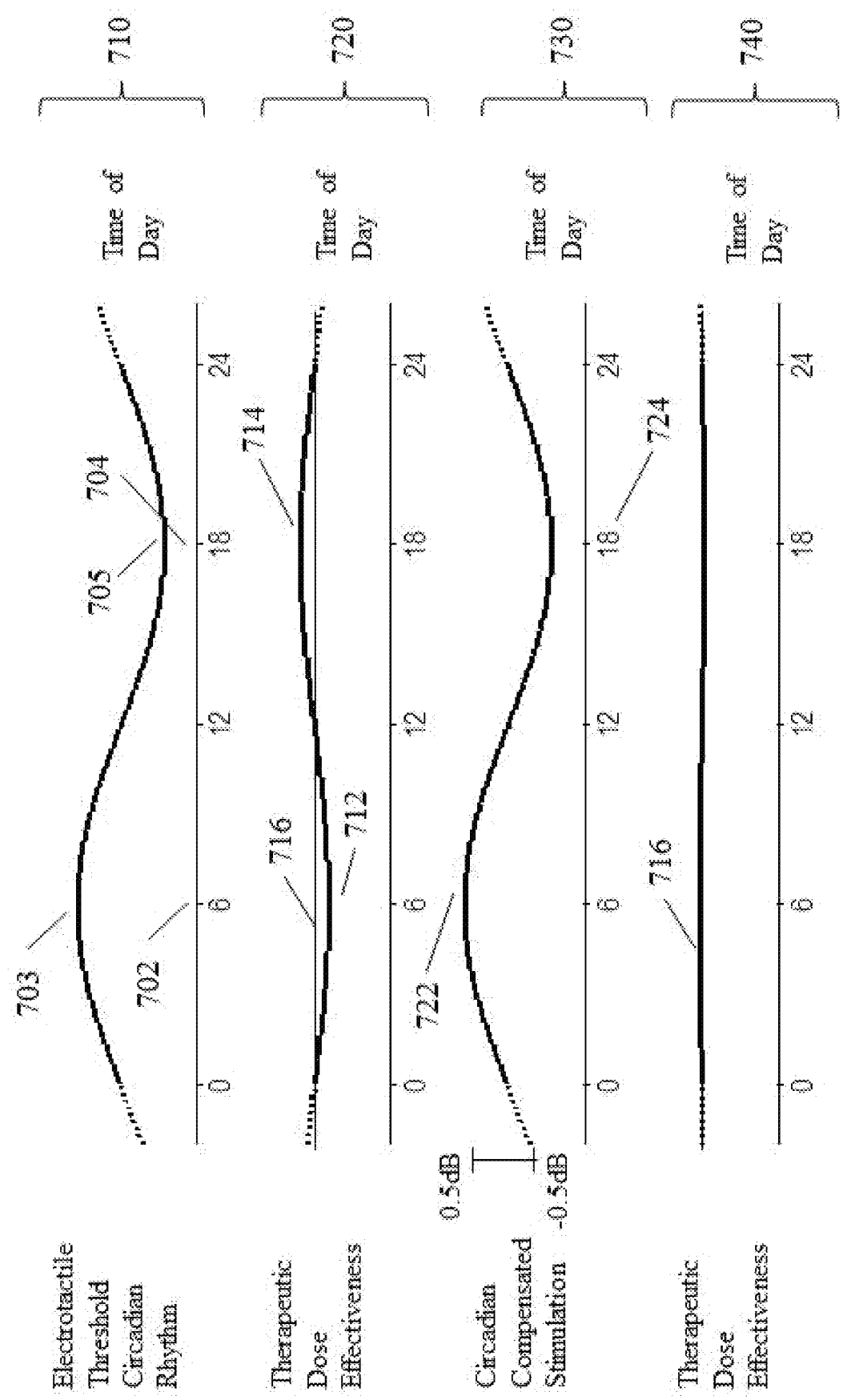
FIG. 7 is schematic view showing an example of the use of a circadian compensation function to compensate for the impact of circadian rhythm on the electrotactile perception threshold.

FIG. 7 shows how the CCF corrects for the impact of a circadian rhythm on the electrotactile perception threshold for an exemplary user. The top graph 710 shows a 24-hour circadian rhythm of the electrotactile perception threshold. In this example, the electrotactile perception threshold is at maximum at 6:00 AM (702) and a minimum at 6:00 PM (704). The second graph 720 shows the impact of circadian variation in the electrotactile perception threshold on the effective stimulation intensity for a constant stimulation intensity. The horizontal line 716 represents the target stimulation level, which in the absence of temporal variation in the electrotactile perception threshold would result from constant stimulation intensity. Values above the horizontal 716 indicate an effective stimulation intensity above the target stimulation level and values below the horizontal 716 indicate an effective stimulation intensity below the target stimulation level. When the electrotactile perception threshold 710 is at its maximum 703 (i.e., at 6:00 AM, indicated at 702 in FIG. 7), the effective stimulation intensity is at a minimum 712 because fewer nerve fibers are stimulated or their integrated signal in the CNS is attenuated (i.e., due to modulation of the stimulation intensity to take into account the effects of circadian rhythm). Conversely when the electrotactile threshold is at its minimum 705 (i.e., at 6:00 PM, indicated at 704 in FIG. 7), the effective stimulation intensity is at its maximum 714. This is because more nerve fibers are stimulated or their integrated signal in the CNS is amplified (i.e., due to modulation of the stimulation intensity to take into account the effects of circadian rhythm). The third graph 730 shows the CCF derived from Equation 1 for this particular circadian rhythm 710. The CCF function has maximum 722 and minimum 724 times (i.e., 6:00 AM and 6:00 PM, respectively) which match the underlying circadian rhythm 710. In this example, we assume A=0.5 dB so the CCF scales from a maximum 722 of 0.5 dB to a minimum 724 of −0.5 dB. The bottom graph 740 shows the effective stimulation intensity after modulation by the CCF 730 (i.e., after fluctuations in stimulation modulation resulting from circadian rhythm have been corrected for by applying CCF 730 to a default constant stimulation intensity). The effective stimulation intensity 740 now approximates the target stimulation level 716 throughout the entire 24-hour period.

The circadian compensation function (CCF) represented in Equation 1 can be expanded to account for more than one simultaneous sinusoidal circadian rhythm, with each of the multiple simultaneous sinusoidal circadian rhythms being approximated by a sinusoid as represented in Equation 3, $$\Delta(t) = \Sigma_{i=1}^{N} A_i \sin(\omega t + \delta_i) \qquad \text{Eq. 3}$$

Where $A_i$ is the amplitude and $\delta_i$ is the phase of the $i^{th}$ circadian rhythm. This generalized model makes a number of assumptions. Most notably, this generalized model assumes that the impact of multiple circadian rhythms on TENS are independent. As a result, the individual circadian compensation functions can be summed to create a composite circadian compensation function that will compensate for the integrated effect of the individual circadian rhythms. This is a reasonable first order approximation. The more generalized model can be written as shown in Equation 4, $$\Delta(t) = A \sin(\omega t + \varphi) \qquad \text{Eq 4.}$$

where A and $\varphi$ are functions of both $\{A_1 \ldots A_N\}$ and $\{\delta_1 \ldots \delta_N\}$. In one form of the invention, the individual circadian rhythms may not have an independent effect on TENS. In other words, there may be cross-interactions between the individual circadian rhythms.

Figure 8:
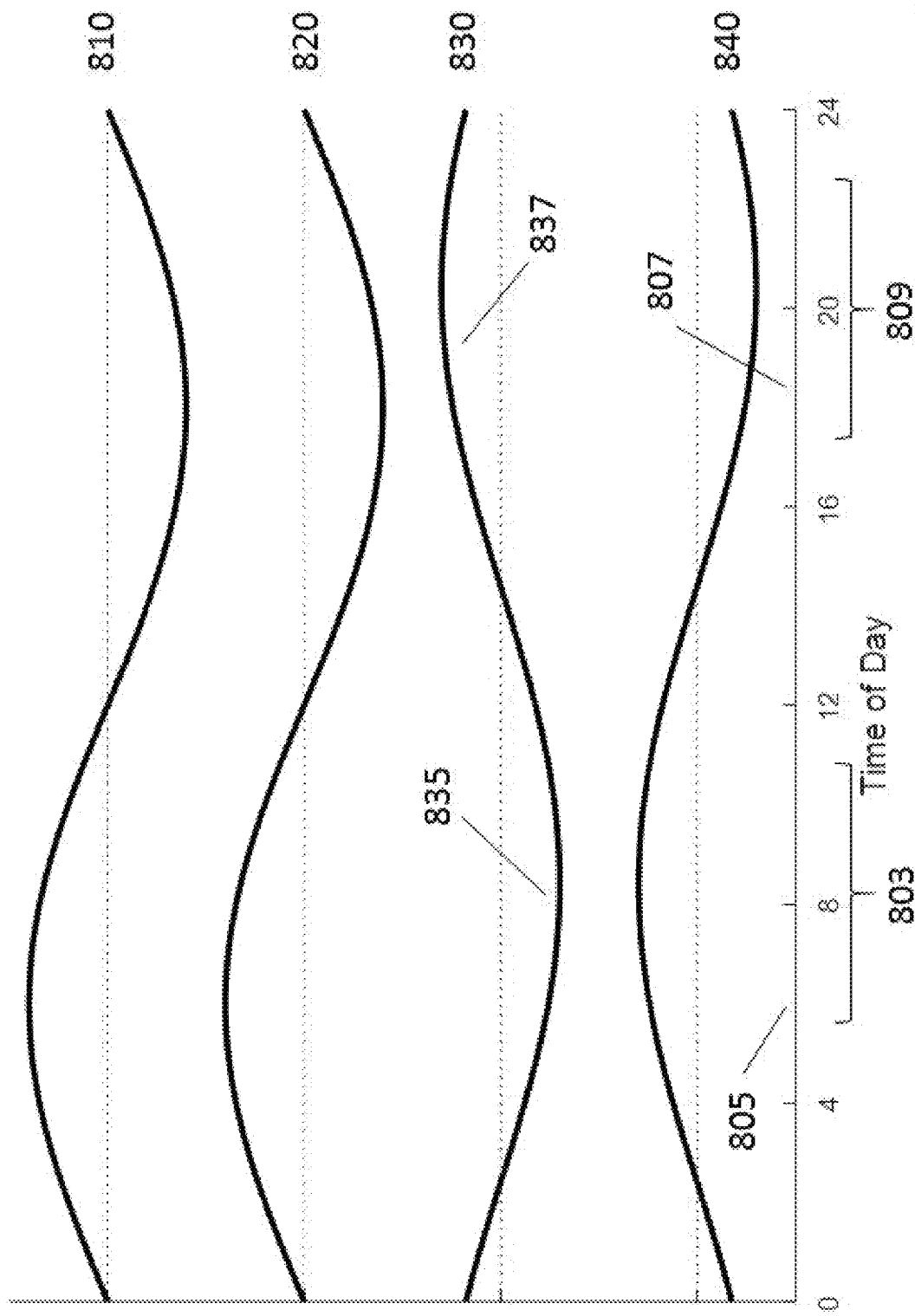
FIG. 8 is a schematic view showing exemplary adjustments to more than one stimulation parameter in order to compensate for the effect of circadian rhythm on the electrotactile perception threshold and pain intensity.

In one preferred form of the invention, circadian compensation of multiple circadian rhythms is accomplished through modulation of one stimulation parameter, such as stimulation pulse intensity. In another preferred form of the invention, circadian compensation is achieved through modulation of multiple stimulation parameters (e.g., stimulation pulse intensity and time delay between stimulation sessions). An example is illustrated via FIG. 8. As shown in FIG. 8, an exemplary user's electrotactile perception threshold circadian rhythm 810 is determined through objective physiological measurement (e.g., Galvanic skin response or skin impedance from a Galvanic response detector, as will hereinafter be discussed in further detail). Accordingly, stimulation intensity 820 is modulated to peak around 805 (i.e., Hour 6 or 6:00 AM) and to bottom around 807 (i.e., Hour 18 or 6:00 PM) whereby to maintain the "strong yet comfortable" TENS stimulation sensation. The pain intensity pattern 830, determined from subjective feedback from the user, is most intense 837 in the evening time period 809 and least intense 835 in the morning time period 803. In order to provide appropriate TENS therapy doses that match the pain intensity pattern 830 under the condition that the electrotactile perception threshold 810 is out of phase with the pain intensity pattern 830, a second stimulation parameter is modulated. By way of example but not limitation, the second stimulation parameter is the time period between two consecutive therapy sessions (i.e., the stimulation session gap) 840; a shorter period is used in the evening time 809 and a longer period is used in the morning 803.

Exemplary Operation for Circadian Compensation

In one preferred form of the invention, TENS device 100 comprises a circadian rhythm processor 515 and a controller 520. TENS device 100 is configured/programmed to operate in the manner shown in FIG. 4.

More particularly, when TENS device 100 is secured to the upper calf 140 of the user and turned on, processor 515 collects data from accelerometer 172, real-time clock 505, temperature sensor 107, ambient light detector 510, and skin impedance and Galvanic response detector 109. Time from real-time clock 505 is used to determine the compensation values. User state (e.g., active, asleep, rest) based on accelerometer 172 and/or other sensors (e.g., light detector 510, temperature sensor 107, etc.) can also be used to determine the compensation values at a given time.

A compensation profile is created by processor 515 using a pre-loaded compensation profile which is universal to all TENS users (i.e., a pre-loaded compensation profile which is already stored in TENS device 100, i.e., in appropriate hardware and software of the sort well known in the art). The pre-loaded compensation profile can also be based on disease state transmitted from a user input module 512 or pain intensity profile transmitted from user input module 512. It should be appreciated that user input module 512 may comprise a data connection (e.g., a USB cable) tethered to an external computer, a wireless connection to a smartphone 860 configured with appropriate software for permitting user input and wirelessly communicating with TENS device 100, etc.). The compensation profile can be based on (or updated in response to) physiological measurements from skin temperature sensor 107, or the skin impedance and a Galvanic response detector 109 (FIG. 4). The compensation profile can be updated by the processor 515 based on input from user input module 512 indicating perceived stimulation intensity (too strong, not strong enough) or indicating the pain intensity at various time instances. The compensation profile is used by processor 515 to calculate a compensation value (e.g., a circadian compensation function).

The compensation value calculated by the processor 515 is transmitted to the controller 520. The controller 520 in turn modifies one or more stimulation parameters such as stimulation pulse intensity, pulse width, pulse frequency, therapy session duration, or the time delay between sessions in order to deliver the optimal and stable pain control.

Data from skin impedance and Galvanic response detector 109, temperature sensor 107, or accelerometer 172 can be used to determine the pain-relieving effect of the TENS stimulation. By way of example but not limitation, more restful sleep at night can be quantified by the accelerometer data (i.e., since more restful sleep results in less movement of the user's body). If sleep measurements improve with the introduction of a modification to the circadian compensation profile, then the processor 515 can incorporate that information to strengthen the modification. If the sleep quality degenerates with a change to the compensation profile, processor 515 may discount the change to the compensation profile.

Figure 9:
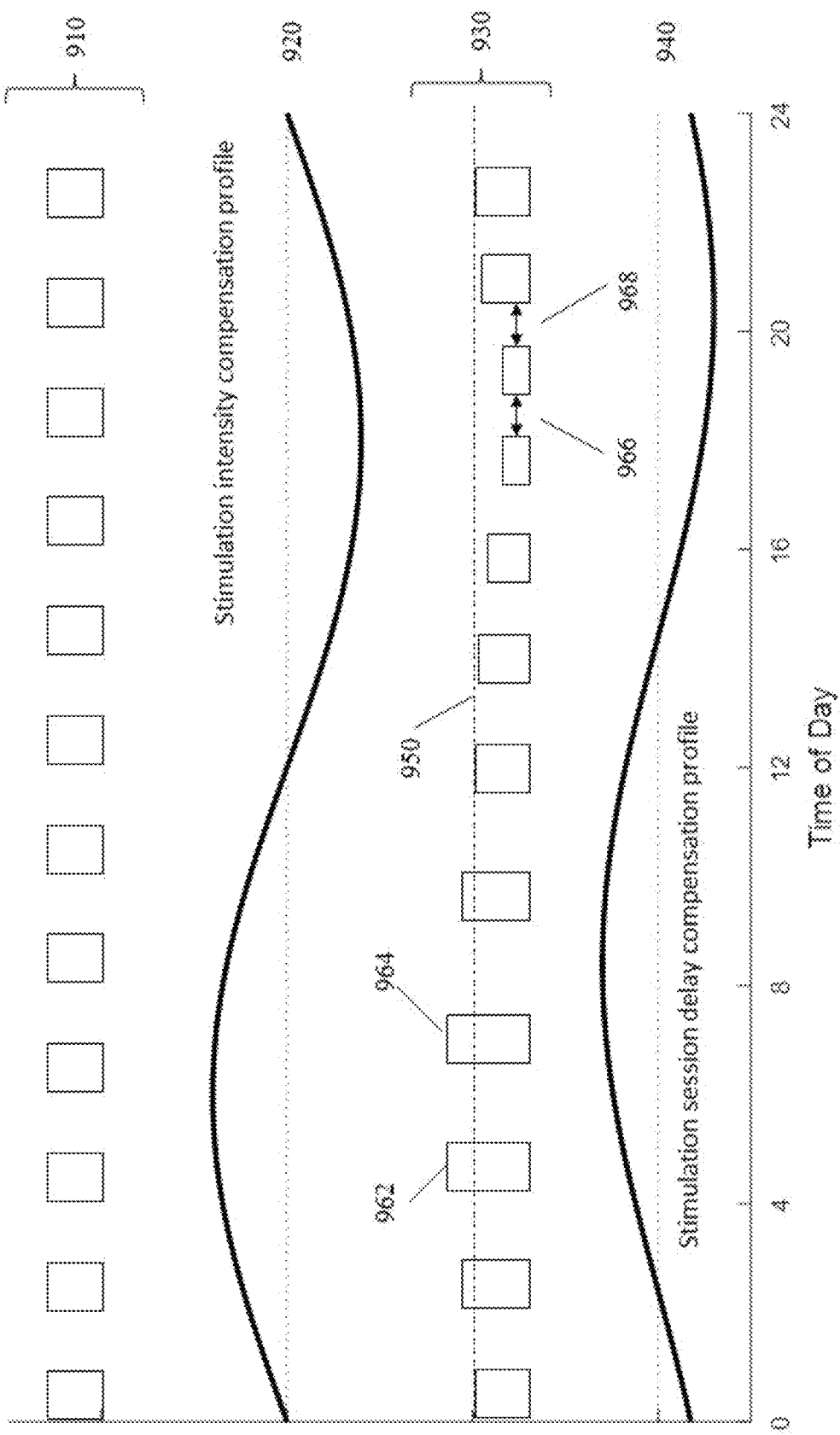
FIG. 9 is a schematic view showing an example of TENS therapy session stimulation patterns after circadian compensations have been applied to the stimulation intensity and the time delay between TENS therapy sessions.
Figure 10:
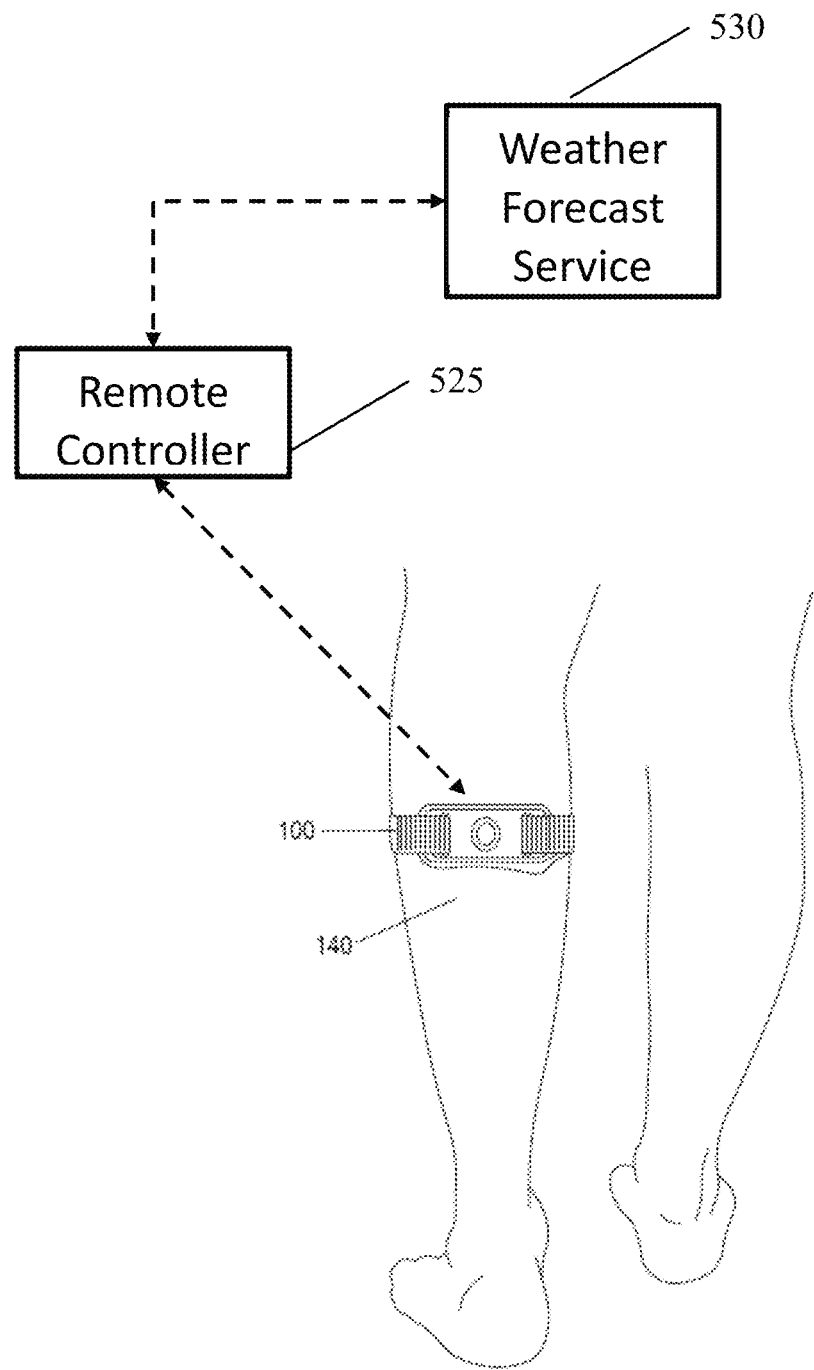
FIG. 10 is a schematic view showing a novel TENS device formed in accordance with the present invention, wherein the novel TENS device is configured for automated control of transcutaneous electrical nerve stimulation based on current and forecasted weather conditions, and further wherein the novel TENS device is mounted to the upper calf of a user.
Figure 11:
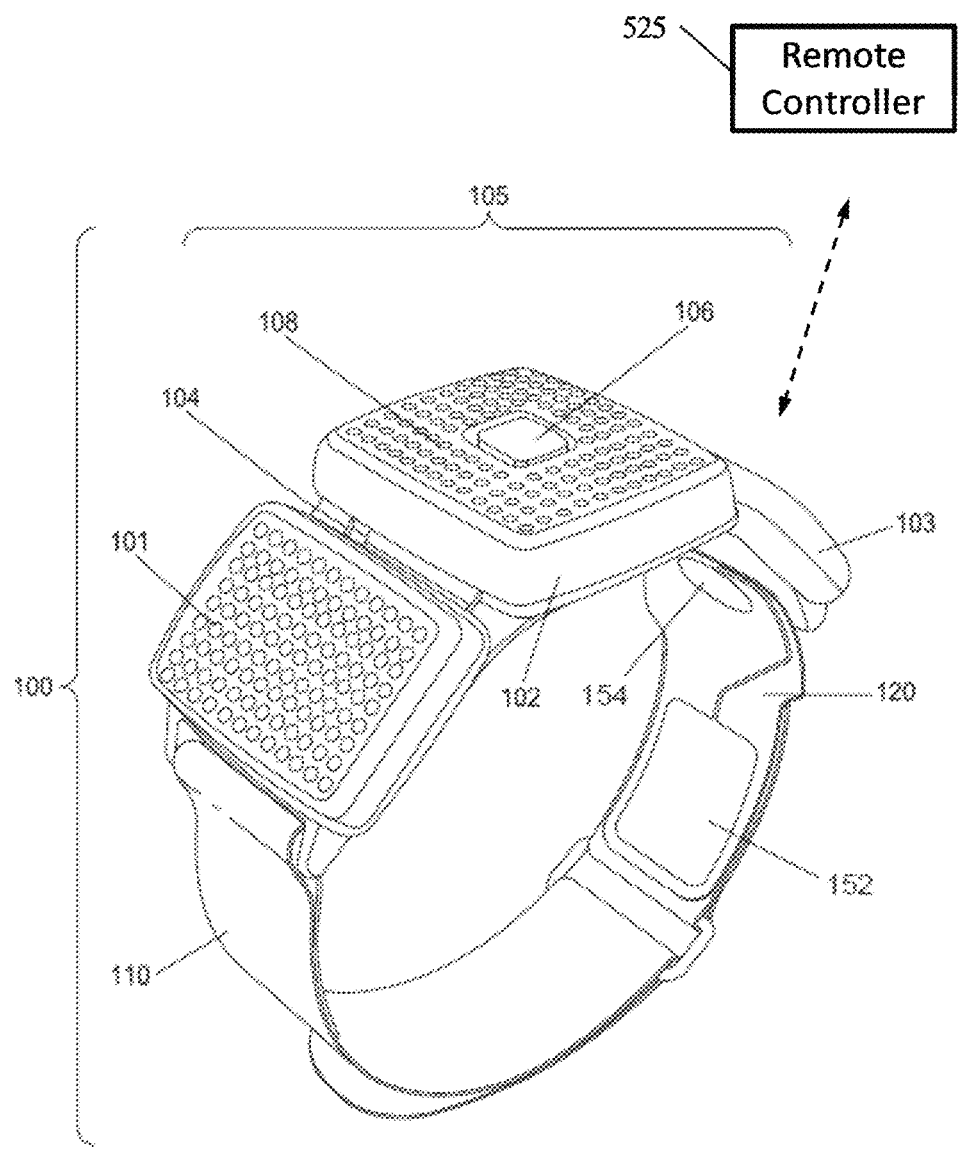
FIG. 11 is a schematic view showing the novel TENS device of FIG. 10 in greater detail.
Figure 12:
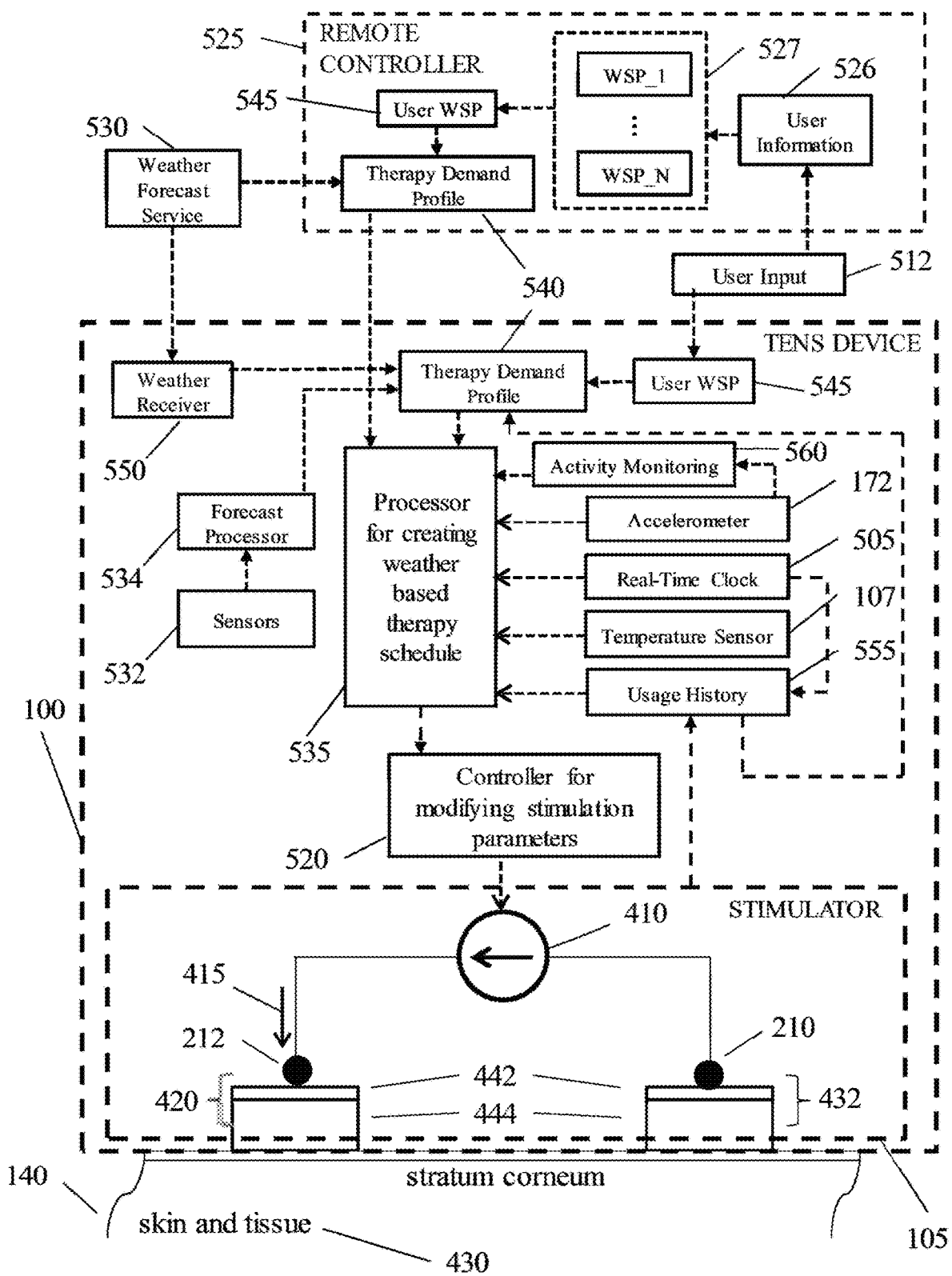
FIG. 12 is a schematic view of the novel TENS device of FIGS. 10 and 11, including its processor for creating a weather-based therapy schedule.

FIG. 9 illustrates the impact of the compensation profiles on TENS therapy session behavior on a 24-hour scale. Boxes 910 represent 12 therapy sessions each of one-hour duration with a fixed stimulation intensity and one-hour delay between consecutive sessions. The height of each box corresponds to the stimulation intensity (however, it should be appreciated that boxes 910 are not necessarily drawn to scale). Stimulation intensity compensation profile 920, which is the same as the aforementioned stimulation intensity profile 820 shown in FIG. 8, peaks (i.e., reaches its maximum value) in the morning due to higher electrotactile perception threshold 810. The stimulation intensity compensation profile 920 reaches its minimum value in the evening. The therapy session delay compensation profile 940, which is the same as the aforementioned stimulation session gap 840 shown in FIG. 8, is shortest in the evening and longest in the morning to match the pain-relieving dose requirement corresponding to a pain intensity profile 830. Boxes 930 represent therapy sessions modulated by the two compensation profiles 920 and 940. The compensation profile 920 causes the stimulation intensity to increase from its default value (indicated by dash line 950), as evidenced by sessions 962 and 964, in order to match higher electrotactile perception threshold in the early morning period. Similarly, the stimulation intensity is smaller than the default level in the evening. The compensation profile 940, on the other hand, causes the period between therapy sessions to change from the default one-hour value. The periods 966 and 968 are shorter than one-hour, leading to more frequent therapy sessions in order to match the requirements of a higher pain intensity experienced by the user in the evening.

TENS Therapy Control Based on Current and Forecasted Weather Conditions

People with chronic pain frequently report that the weather influences their pain. In some cases, pain fluctuates concurrently with the weather and/or other environmental factors. For example, it is common to hear people complain of more pain in cold weather. In other cases, upcoming changes in the weather appear to influence pain more than the actual current weather conditions. Various weather conditions have been shown to impact pain, including temperature, humidity, barometric pressure, wind, and precipitation.

One object of the present invention is to enable the TENS device to automatically adjust the TENS stimulation therapy schedule to counter projected pain severity changes due to current and forecasted changes in weather conditions and/or environmental factors for those TENS users with weather sensitivity. The term "schedule" refers to not only the timing of TENS stimulation therapies but also other controllable TENS stimulation therapy properties that impact the TENS stimulation therapy effectiveness such as stimulation pulse morphology, stimulation pulse amplitude, stimulation pulse width, stimulation pulse frequency, and stimulation session duration. More particularly, in accordance with the present invention, there is provided a novel TENS device 100 (see FIGS. 10-14) which is configured to automatically modulate at least one TENS stimulation parameter to compensate for the effect of weather conditions on the pain perception of a TENS user.

By way of example but not limitation, it is known that barometric pressure change (e.g., barometric pressure falling by 3 mmHg or more over the next 24 hours) may cause a person with chronic knee pain to feel greater pain during that time period. If a TENS user has indicated in their User Weather Sensitivity Profile (WSP) 545 (see below) that falling barometric pressure normally would increase their knee pain, and if the connected Remote Controller 525 (e.g., an App running on a Bluetooth enabled smartphone 860) receives a forecast from Weather Forecast Service 530 of such barometric pressure change within the next 24 hours, a "trigger" will be set on Remote Controller 525 to update the user's Therapy Demand Profile 540. When Remote Controller 525 is connected with TENS device 100 (e.g., via Bluetooth connection), the updated Therapy Demand Profile 540 is sent via the Bluetooth link to TENS device 100. As an example, default Therapy Demand Profile 540 for the user may call for 60 minute therapy sessions every other hour. The updated Therapy Demand Profile 540 (updated via Remote Controller 525) may call for 60 minute therapy sessions with only a 30 minute interval between sessions. The updated Therapy Demand Profile 540 will also specify "effective time window" during which the profile will be in force. The effective time window can be a fixed period of time after the triggering event occurrence (e.g., 24 hours after the barometric pressure drop) or for the duration of the weather condition (e.g., during the time when temperature is below 32 degrees Fahrenheit).

In one preferred embodiment, a user specifies their User Weather Sensitivity Profile (WSP) 545 directly on TENS device 100 via User Input 512. By way of example but not limitation, User Input 512 can be a PC program interfaced with TENS device 100 via a wired connection (e.g., a USB connection) or wireless connection (e.g., a Bluetooth connection). User Input 512 can also be a Radio Frequency Identification (RFID) chip carried by the user (e.g., on a bracelet), with the RFID chip comprising the desired WSP data and appropriate security-pairing information.

In another embodiment, User Input 512 can also be an App running on Remote Controller 525 (e.g., a handheld device such as a smartphone 860) that allows the user to specify one or more weather conditions that impact their pain. Alternatively, the user can select one or more pain-inducing weather patterns from a pre-defined list of pain-inducing weather patterns. In this respect, it should be noted that pain impact can be either increasing pain or decreasing pain. In the case of decreasing pain, a reduced TENS therapy may be implemented by TENS device 100.

In yet another embodiment, a user specifies User Information 526 (including demographic information such as age, gender, weight, and height, and clinical information such as pain location, pain history, and pain pattern) via User Input 512.

Remote Controller 525 matches user-entered information with those associated with a collection of Weather Sensitivity Profiles (WSP) 527 to select the best matched User WSP 545 based on User Information 526. The determination of the best matched User WSP 545 can be accomplished by pattern recognition methods such as the "nearest neighbor pattern matching method".

Associations between User Information 526 and User WSP 545 can be updated and fine-tuned by the user. For example, an association between people with osteoarthritis and temperature drop is specified for either gender with a common temperature drop threshold. It is known that women are more sensitive to temperature drop. Therefore, female users will be more likely to indicate their sensitivity to temperature drop in their User WSP 545 in the presence of a smaller temperature drop than their male counterpart by changing the temperature drop threshold in their User WSP 545. In one preferred embodiment, associations between User Information 526 and the User WSP 545 are collected from multiple users and stored on a common networked storage device (e.g., cloud storage). Data analytics can be performed on association patterns between the collection of User WSP 545 and individual aspects of User Information 526 to uncover statistically and clinically meaningful correlations. These correlations can then be used to create a customized WSP Collection 527 for individual users based on their User Information 526 provided. Note that it is also possible to leverage uncovered correlations to further refine User WSP 545, through either feedback to individual users prompting them to update their User WSP 545 manually or through an automated User WSP update. If it is determined that female TENS users indicate their sensitivity to smaller temperature drops than their male counterparts, then for future TENS users, a smaller temperature drop threshold is set for female users than for male users if gender information is specified in User Information 526.

It is worth noting that weather information from Weather Forecast Service 530 refers to the weather specific to the current location of the user as specified by the user or as determined by a location sensing device (e.g., such as Sensors 532) embedded in TENS device 100 or Remote Controller 525. Furthermore, weather condition information includes that from the recent past (past few days), current, and near future (next few days).

Weather Forecast Service 530 can be a national weather service, regional weather service, local weather station, or home-based weather station. Weather information applicable to user location is selected if the Weather Forecast Service 530 provides weather information for more than one location. In one preferred embodiment, Remote Controller 525 receives localized weather information from a national weather service via the Internet and determines if one or more pre-determined "pain inducing" weather patterns from User WSP 545 are present in the received weather information. If one or more such "pain inducing" weather patterns are identified, Remote Controller 525 update Therapy Demand Profile 540 and send the update to Process 535 on TENS device 100. Processor 535 is configured to alter the therapy schedule based on the updated Therapy Demand Profile 540. For example, if the default Therapy Demand Profile 540 calls for a 60-minute therapy session starting every two hours, and if the updated Therapy Demand Profile calls for therapy sessions every 90 minutes, then Processor 535 will change the restart timer (a part of Real-Time Clock 505) to 90 minute intervals from 120 minute intervals. Note that in one preferred form of the invention, processor 535 comprises a general purpose central processing unit (CPU) with appropriate programming to function as described herein.

In another preferred embodiment, a Weather Receiver 550 is embedded in TENS device 100. Weather Receiver 550 receives indoor/outdoor weather and ambient conditions from Weather Forecast Service 530. Weather Forecast Service 530 can be a national weather service, regional weather service, local weather station, or home-based weather station. Using the example of a home weather station (e.g., Ambient Weather WS-2902), Weather Receiver 550 receives local weather and ambient conditions from the home weather station via a local WiFi network. If a previously downloaded User WSP 545 specifies that a pain-inducing condition is ambient humidity above 85% and an ambient temperature above 92 degrees Fahrenheit, and if the current ambient weather conditions received by Weather Receiver 550 meet the two foregoing criteria, Therapy Demand Profile 540 is then modified.

It is worth noting that while Therapy Demand Profile 540 may be specified as an absolute parameter (e.g., a 120 minute therapy session interval versus a 90 minute therapy session interval), the Therapy Demand Profile 540 can also be specified in relative terms. By way of example but not limitation, the aforementioned high humidity and high temperature conditions could trigger a 20% increase in the default therapeutic current intensity (Pulse Amplitude 493). Processor 535 will thus alter this stimulation parameter (i.e., therapeutic current intensity) by increasing the regular Pulse Amplitude value 493 by 20% until either the humidity or temperature level falls below the specified threshold. The regular Pulse Amplitude 493 value (i.e., the therapeutic current intensity) can be extracted from Usage History 555 which tracks the actual TENS therapy utilization history.

In yet another preferred embodiment, Sensors 532 comprise a temperature sensor, a moisture sensor, and a barometric pressure sensor. These Sensors 532 sample the environment immediately adjacent to the TENS user wearing TENS device 100 on their upper calf. Measurement data from Sensors 532 are sent to Forecast Processor 534 running weather forecast algorithms. The Forecast Processor 534 compares past and current sensor data and determines likely future weather patterns and environmental conditions. Therapy Demand Profile 540 combines information from User SWP 545 and Forecast Processor 534 to obtain an updated Therapy Demand Profile 540. The update Therapy Demand Profile 540 is then used by Processor 535 to modify the TENS therapy schedule (e.g., by modifying the performance of controller 520) to counteract the change in pain due to upcoming weather changes.

In one preferred embodiment, factors other than weather conditions are used by Processor 535 to determine the therapy schedule. Staying active and regular exercise reduce chronic pain severity. Weather conditions such as cold or rainy days can increase pain perception of some chronic pain sufferers. Additionally, poor weather conditions could limit the activity of chronic pain sufferers by preventing them from carrying out their routine exercises. Using data from Accelerometer 172, Activity Monitoring Unit 560 can track the activity levels of TENS users. With the activity level information from Activity Monitoring 560, different therapy schedules can be created by Processor 535 for the same Therapy Demand Profile 540 based on the same weather forecast conditions and user weather sensitivity profile: on days a TENS user engages in a higher level of activities (e.g., through shopping activities in a shopping mall), a smaller increase in TENS therapy dose is needed. This may be accomplished by Processor 535 setting a slightly increased therapy schedule (e.g., an increase in the therapy duty cycle from 50% to 60%), as compared with a day when the activity level of the TENS user is very low (e.g., confined to home due to the same poor weather condition), in which case Processor 535 may set a more significant increase in the therapy schedule (e.g., the therapy duty cycle is increased to 75% from 50%).

Stated another way, in accordance with the present invention, TENS device 100 may comprise a Processor 535 for creating a weather-based therapy schedule. Processor 535 communicates with Controller 520 for modifying the stimulation parameters of constant current source 410 of stimulator 105. Processor 535 uses the Therapy Demand Profile 540, Activity Monitoring 560, Accelerometer 172, Real-Time Clock 505, Temperature Sensor 107 and Usage History 555 to appropriately operate Controller 520, whereby to appropriately modulate constant current source 410. Note that Therapy Demand Profile 540 may comprise a default Therapy Demand Profile 540 or an updated Therapy Demand Profile 540. Note also that Therapy Demand Profile 540 may be adjusted using User WSP 545, remote controller 528, Weather Receiver 550, Sensors 532/Forecast Processor 534, and Usage History Unit 555.

A User Input 512 may be used to supply information to User WSP 545 and/or User Information 526.

Exemplary Operation for Weather Controlled Therapy

In one preferred form of the invention, TENS device 100 comprises the Processor 535 (for creating a weather-based therapy schedule) and the Controller 520 (for modifying stimulation parameters based on the therapy schedule). TENS device 100 is configured/programmed to operate in the manner shown in FIG. 12.

More particularly, when TENS device 100 is secured to the upper calf 140 of the user and turned on, Processor 535 collects data from Accelerometer 172, Real-Time Clock 505, and Usage History 555. Time data from Real-Time Clock 505 is used to determine the therapy schedule and the historical therapy usage patterns stored in Usage History 555. Therapy Demand Profile 540 can be determined based on User WSP 545 and the weather information received from Weather Receiver 550. Therapy Demand Profile 540 can also be updated in Remote Controller 525 based on User WSP 545 and the weather information provided by Weather Forecast Service 530 via a wireless network.

The default values of Therapy Demand Profile 540 are pre-loaded at the factory. They can be updated with user-specific values from Usage History 555. Therapy Demand Profile values can also be based on User WSP 545 as provided via User Input 512. It should be appreciated that User Input 512 may comprise a data connection (e.g., a USB cable) tethered to an external computer, or a wireless connection to Remote Controller 525 configured with appropriate software for permitting user input and wirelessly communicating with TENS device 100 (e.g., a smartphone running an App and connected to TENS device 100 via a Bluetooth connection), etc. User Weather Sensitivity Profile (WSP) 545 can be directly specified by a user via User Input 512. User WSP 545 can also be selected by a user from a pre-defined Collection of WSP 527. User WSP 545 can also have been constructed based on User Information 526 as provided via User Input 512 and associations between features in User Information 526 and a Collection of WPS 527. User WSP 545 can be further refined based on feedback by the user after experiencing weather conditions that impact their pain severity. When forecasted weather conditions from Weather Forecast Service 530 match one or more conditions specified in User WSP 545, an update to Therapy Demand Profile 540 is triggered. The update is communicated to Process 535 automatically via a communication link (such as Bluetooth Communications Link) between Remote Controller 525 and TENS device 100. Alternatively, the user may be prompted to accept, modify, or decline the proposed update. Changes to Therapy Demand Profile 540 last for a pre-determined period as specified in User WSP 545. After that, Therapy Demand Profile 540 returns to its weather neutral state. In this way, relevant weather patterns will cause transient changes in therapy dose to counteract the effect of weather on pain perception.

Therapy Demand Profile 540 is used by Processor 535 to create a therapy schedule for Controller 520. Controller 520 in turn modifies one or more stimulation parameters such as stimulation pulse intensity, pulse width, pulse frequency, therapy session duration, or the time delay between sessions in order to deliver the optimal and stable pain control.

Figure 13:
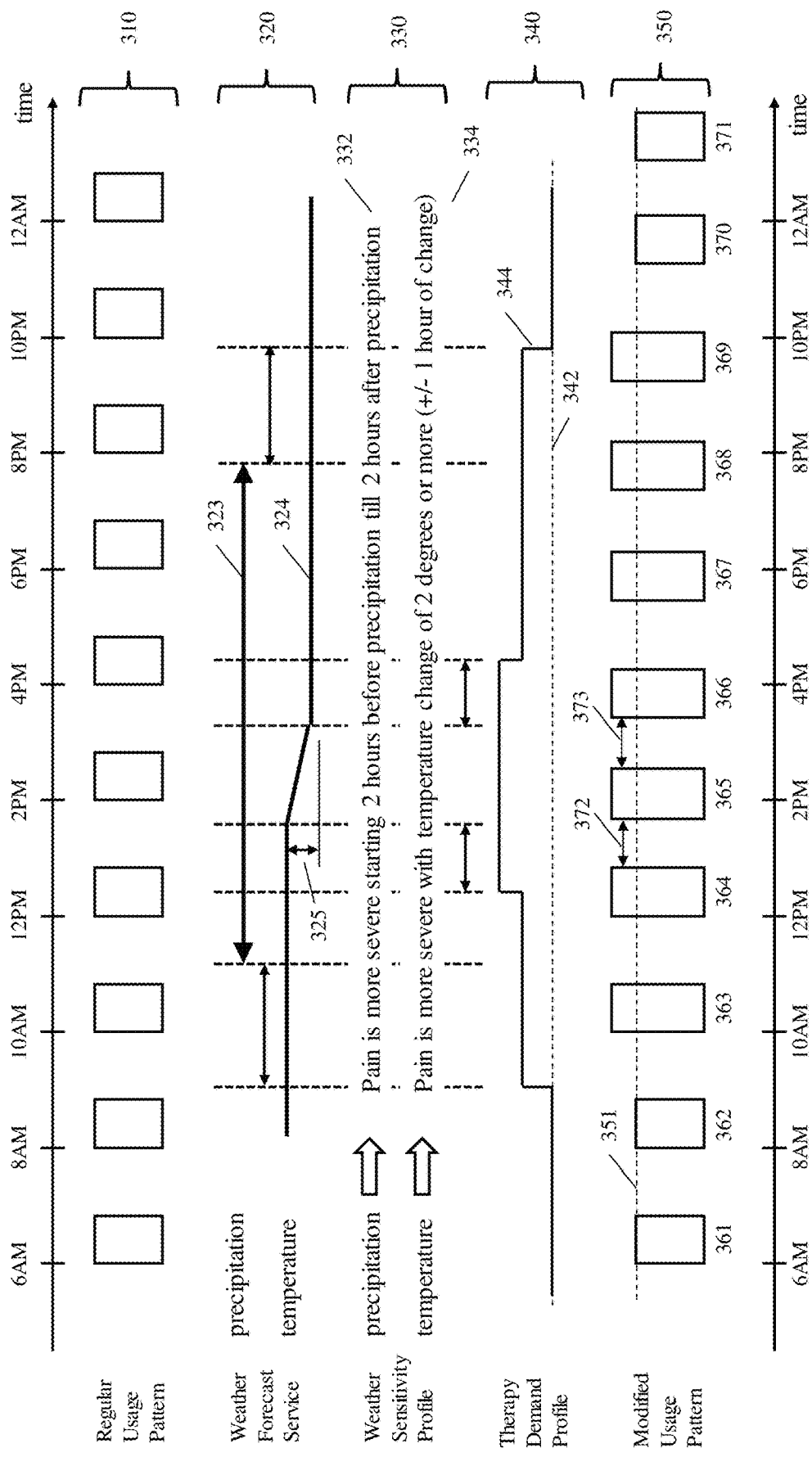
FIG. 13 is a schematic view showing an example of TENS therapy session stimulation patterns after weather forecast conditions have been applied to a weather sensitivity profile to create a therapy schedule designed to counteract the effects of weather-induced pain.

FIG. 13 shows an exemplary case to illustrate the impact of weather forecast on TENS therapy session behavior for a TENS user with weather sensitivity. Boxes 310 in FIG. 13 represent 11 therapy sessions, corresponding to a user's regular daily usage pattern, each of one hour duration with a fixed stimulation intensity and one hour delay between consecutive sessions. The height of each box 310 corresponds to the stimulation intensity (however, it should be appreciated that boxes 310 are not necessarily drawn to scale). At midnight, Weather Forecast Service 530 provides precipitation and temperature forecast 320 at the user's location: precipitation 323 is expected between 11:00 am to 8:00 pm and temperature 324 is expected to drop by 3 degrees Fahrenheit 325 from 1:30 pm to 3:30 pm. Based on User Input 512, User WSP 545 is specified as shown at 330 in FIG. 13 for precipitation 332 and temperature change 334. Therapy Demand Profile 340 has the default value 342 (FIG. 13) throughout the day (i.e., the default Therapy Demand Profile 540). A higher TENS therapy dose is to be delivered to counter weather-induced pain increases when the weather forecast conditions match those specified in User WSP 545. Updated Therapy Demand Profile 540 is shown as 344 in FIG. 13. The updated Therapy Demand Profile 540 increases the therapy dose 2 hours ahead of the anticipated onset of precipitation at 9:00 am. The updated Therapy Demand Profile 540 further increases the therapy dose 1 hour before the forecasted temperature drop at 12:30 pm. One hour after the temperature drop ends, the TENS therapy dose requirement is relaxed to a lower level at 4:30 pm. Finally, at 10:00 pm (2 hours after the end of precipitation), the therapy dose returns to its baseline value (i.e., the updated Therapy Demand Profile 540 returns to its default Therapy Demand Profile 540). Boxes 350 in FIG. 13 represent therapy sessions (sessions 361-371) modulated by the Controller 520 in response to Therapy Demand Profile 0344. The initial increase of Therapy Demand Profile 344 at 9:00 am causes the stimulation intensity to increase from its default value (indicated by the dashed line 351), as evidenced by sessions 363 and 364, in order to deliver the higher therapy dose needed to counteract the "pain-inducing" precipitation condition. A further increase of Therapy Demand Profile 344 at 12:30 pm causes a shortening of intervals between therapy sessions 364 and 365 (interval 372) and between sessions 365 and 366 (interval 373). After 4:30 pm, updated Therapy Demand Profile 540, shown as 344 in FIG. 13, begins to relax to a lower level, causing the intervals between therapy sessions to return to their baseline value. However, the stimulation intensity remains above the baseline level 351 until 10:00 pm. Then the updated Therapy Demand Profile 540, shown as line 344 in FIG. 13, returns to its baseline after 10:00 pm, and both stimulation intensity and session intervals return to their baseline levels.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. Apparatus for delivering transcutaneous electrical stimulation to a user, the apparatus comprising:
    a stimulator for electrically stimulating at least one part of the user body;
    a controller connected to said stimulator for controlling at least one characteristic of the stimulation delivered by the stimulator; and
    an analyzer for identifying the presence of a pattern, wherein the pattern is based on at least one weather condition or environmental factor, wherein the at least one weather condition or environmental factor is provided by a weather service provider;
    wherein the controller uses the pattern identified by said analyzer to automatically modify at least one characteristic of the stimulation.

2. Apparatus according to claim 1 wherein said stimulator stimulates the user with at least one stimulation pulse.

3. Apparatus according to claim 1 wherein the at least one characteristic of the stimulation comprises at least one from the group consisting of stimulation pulse amplitude; stimulation pulse width; total charge of the stimulation pulse; frequency at which stimulation pulses are generated.

4. Apparatus according to claim 1 wherein the at least one characteristic of the stimulation comprises the duration of a therapy session during which stimulation pulses are generated.

5. Apparatus according to claim 1 wherein the at least one characteristic of the stimulation comprises the time between two consecutive therapy sessions.

6. Apparatus according to claim 1 wherein the weather and/or environmental factors comprise at least one selected from the group consisting of: past weather and/or environmental conditions, current weather and/or environmental conditions, and predicted future weather and/or environmental conditions.

7. Apparatus according to claim 1 wherein the weather and/or environmental factors comprise at least one selected from the group consisting of: temperature, precipitation, humidity, barometric pressure, and wind speed.

8. Apparatus according to claim 1 wherein the pattern causes onset of pain perceived by the user.

9. Apparatus according to claim 1 wherein the pattern causes a change of pain experienced by the user.

10. Apparatus according to claim 1 wherein the pattern includes at least one selected from the group consisting of: a temperature below a temperature threshold, a humidity above a humidity threshold, a wind speed exceeding a wind speed threshold, a precipitation amount exceeding a precipitation amount threshold, and a barometric pressure below a barometric pressure threshold.

11. Apparatus according to claim 10 wherein the value of at least one of the temperature threshold, humidity threshold, wind speed threshold, precipitation amount threshold and barometric pressure threshold depends on at least one selected from the group consisting of: demographic information of the user and a health condition of the user.

12. Apparatus according to claim 11 wherein the health condition of the user comprises at least one selected from the group consisting of: pain history, pain location, pain duration, pain frequency, pain pattern, and weather sensitivity.

13. Apparatus according to claim 11 wherein the demographic information of the user comprises at least one selected from the group consisting of: age, gender, height, and weight.

14. Apparatus according to claim 1 wherein the pattern includes the rate of change of at least one of the weather and/or environmental factors exceeding a pre-determined threshold.

15. Apparatus according to claim 1 wherein said controller modifies the at least one characteristic of the stimulation concurrently with the presence of the pattern based on weather and/or environmental factors.

16. Apparatus according to claim 1 wherein said controller modifies the at least one characteristic of the stimulation prior to the presence of the pattern based on weather and/or environmental factors.

17. Apparatus according to claim 1 wherein said controller modifies the at least one characteristic of the stimulation for a fixed time period.

18. Apparatus according to claim 1 wherein said controller modulates the at least one characteristic of the stimulation for the same duration as the patterns based on weather and/or environmental factors.

19. Apparatus according to claim 1 further comprising:
at least one sensor for measuring weather and/or environmental factors;
wherein said at least one sensor is connected to said analyzer, and further wherein the pattern is determined based on weather and/or environmental factors measured by the at least one sensor.

20. Apparatus according to claim 19 wherein said at least one sensor comprises at least one selected from the group consisting of: a temperature sensor, a humidity sensor, and a barometric pressure sensor.

21. Apparatus according to claim 19 wherein the pattern includes at least one selected from the group consisting of: a temperature below a temperature threshold, a humidity above a humidity threshold, and a barometric pressure below a barometric pressure threshold.

22. Apparatus according to claim 21 wherein the value of at least one of the temperature threshold, the humidity threshold, and the barometric pressure threshold depends on at least one selected from the group consisting of: demographic information of the user and a health condition of the user.

23. Apparatus according to claim 19 wherein the pattern includes the rate of change of at least one of the weather and/or environmental factors exceeding a pre-determined threshold.

24. Apparatus according to claim 1 further comprising:
a monitor for measuring the activity level of the user;
wherein the monitor is connected to said controller, and further wherein said controller modifies the at least one characteristic of the stimulation according to the pattern identified by said analyzer and the activity level measured by said monitor.

25. Apparatus for delivering transcutaneous electrical stimulation to a user, the apparatus comprising:
a stimulator for electrically stimulating at least one part of the user body;
a controller connected to said stimulator for controlling at least one characteristic of the stimulation delivered by the stimulator; and
an analyzer for identifying the presence of a pattern, wherein the pattern is based on at least one weather condition or environmental factor, wherein the at least one weather condition or environmental factor comprises at least one selected from the group consisting of: past weather and/or environmental conditions, current weather and/or environmental conditions, and predicted future weather and/or environmental conditions;
wherein the controller uses the pattern identified by said analyzer to automatically modify at least one characteristic of the stimulation.

26. Apparatus for delivering transcutaneous electrical stimulation to a user, the apparatus comprising:
a stimulator for electrically stimulating at least one part of the user body;
a controller connected to said stimulator for controlling at least one characteristic of the stimulation delivered by the stimulator; and
an analyzer for identifying the presence of a pattern, wherein the pattern is based on at least one weather condition or environmental factor, wherein the pattern includes the rate of change of at least one of the weather and/or environmental factors exceeding a pre-determined threshold;
wherein the controller uses the pattern identified by said analyzer to modify at least one characteristic of the stimulation.

* * * * *